United States Patent
Al Dhfyan et al.

(10) Patent No.: US 10,550,130 B2
(45) Date of Patent: Feb. 4, 2020

(54) BENZO-THIAZOLO-IMIDAZOLE COMPOUNDS AND USES THEREOF

(71) Applicants: KING SAUD UNIVERSITY, Riyadh (SA); KING FAISAL SPECIALIST HOSPITAL & RESEARCH CENTRE, Riyadh (SA)

(72) Inventors: Abdullah Omar Al Dhfyan, Riyadh (SA); Hatem Abdel-Kader Abdel-Aziz, Riyadh (SA); Pulicat Subramanian Manogran, Riyadh (SA); Monther Mohammad Al-Alwan, Riyadh (SA); Hazem M. Bachir Ghebeh, Riyadh (SA); Kamal El-Din Hussein El-Tahir, Riyadh (SA)

(73) Assignees: King Faisal Specialist Hospital & Research Centre, Riyadh (SA); King Saud University, Riyadh (SA)

( * ) Notice: Subject to any disclaimer, the term of this patent is extended or adjusted under 35 U.S.C. 154(b) by 0 days.

(21) Appl. No.: 15/071,945

(22) Filed: Mar. 16, 2016

(65) Prior Publication Data
US 2016/0272652 A1    Sep. 22, 2016

(30) Foreign Application Priority Data
Mar. 17, 2015    (EP) .................................... 15159402

(51) Int. Cl.
C07D 513/04    (2006.01)
A61K 45/06    (2006.01)
A61K 31/429    (2006.01)

(52) U.S. Cl.
CPC .......... *C07D 513/04* (2013.01); *A61K 31/429* (2013.01); *A61K 45/06* (2013.01)

(58) Field of Classification Search
None
See application file for complete search history.

(56) References Cited

FOREIGN PATENT DOCUMENTS

WO    WO 02/098403 A1 * 12/2002 ............. A61K 31/19

OTHER PUBLICATIONS

Machine Translation via Esp@cenet for CN 101817836A; published Feb. 29, 2012; downloaded Apr. 10, 2017.*
Machine Translation via Google Patents for CN 101817836 A; published Feb. 29, 2012; downloaded Apr. 10, 2017.*
Pece et al.; J. Cell Biology; vol. 167, No. 2, Oct. 25, 2004, pp. 215-221.*
STIC search results; received and downloaded Apr. 10, 2017.*
Tilomisole PubChem search results (https://pubchem.ncbi.nlm.nih.gov/compound/42747); downloaded Apr. 10, 2017.*
Al-Rashood et al.; Molecules; 2010, 15; pp. 3775-3815. Published May 26, 2010.*
Al-Hajj, M. et al., "Prospective identification of tumorigenic breast cancer cells," PNAS, Apr. 1, 2013, pp. 3983-3988, vol. 100, No. 7.
Charafe-Jauffret, E. et al., "Aldehyde Dehydrogenase 1-Positive Cancer Stem Cells Mediate Metastasis and Poor Clinical outcome in Inflammatory Breast Cancer," accr jornals, 2010, pp. 45-55.
Dontu, G. et al., "In vitro propagation and transcriptional profiling of human mammary stem/progenitor cells," Genes & Development, 2003, pp. 1253-1270, vol. 17.
Frank, N. et al., "The therapeutic promise of the cancer stem cell concept," J. of Clin. Invest., Jan. 2010, pp. 41-50, vol. 120, No. 1.
Ginestier, C. et al., "ALDH1 is a Marker of Normal and Malignant Human Mammary Stem Cells and a Predictor of Poor Clinical Outcome," Cell Stem Cell, Nov. 2007, pp. 555-567, vol. 1.
Kondo, T. et al., "Persistence of a small subpopulation of cancer stem-like cells in the C6 glioma cell line," PNAS, Jan. 20, 2004, pp. 781-786, vol. 101, No. 3.
Li, X. et al. "Intrinsic Resistance of Tumorigenic Breast Cancer Cells to Chemotherapy," JNCI, May 7, 2008, pp. 672-679, jvol. 100, No. 9.
McDermott, S. et al., "Targeting breast cancer stem cells," Molecular Oncology, 2010, pp. 404-419, vol. 4.
Morimoto, K. et al., "Stem cell marker aldehyde dehydrogenase 1-positive breast cancers are characterized by negative estrogen receptor, positive human epidermal growth factor receptor type 2, and Ki67 expression," Cancer Sci, Jun. 2009, pp. 1062-1068, vol. 100, No. 6.
Patrawala, L. et al., "Side Population is enriched in Tumorigenic, Stem-Like Cancer Cells, Whereas ABCG2+ and ABCG2− Cancer Cells are Similarly Tumorigenic," Cencer Res, Jul. 15, 2005, pp. 6207-6219, vol. 65, No. 14.
Tanei, T. et al., "Association of Breast Cancer Stem Cells Identified by Aldehyde Dehydrogenase 1 Expression with Resistance to Sequential Paclitaxel and Epirubicin-Based Chemotherapy for Breast Cancers," Clin Cancer REs, Jun. 15, 2009, pp. 4234-4241, vol. 15, No. 12.
Yu, F. et al., "Let-7 Regulates Self Renewal and Tumorigenicity of Breast Cancer Cells," Cell, Dec. 14, 2007, pp. 1109-1123, vol. 131.

* cited by examiner

*Primary Examiner* — Jeffrey T. Palenik
(74) *Attorney, Agent, or Firm* — Saliwanchik, Lloyd & Eisenschenk

(57) ABSTRACT

The present invention provides benzo-thiazolo-imidazole compounds and pharmaceutical compositions comprising such benzo-thiazolo-imidazole compounds and at least one pharmaceutically acceptable carrier, diluent and/or excipient. Further provided are methods of treatment of cancer comprising the administration of said compounds and compositions and methods of using said compounds and compositions for the manipulation of cultured cells.

14 Claims, 27 Drawing Sheets

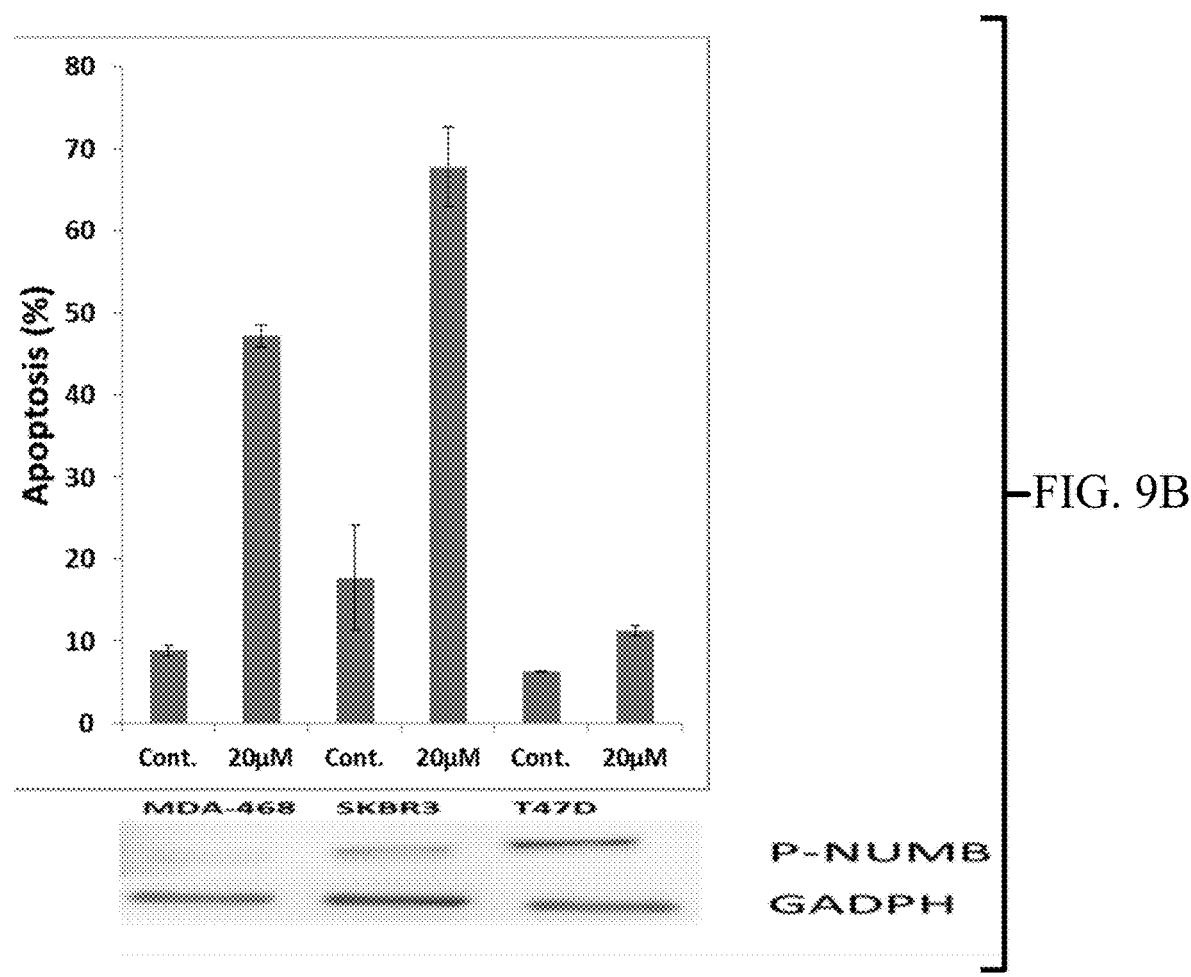

BENZO-THIAZOLO-IMIDAZOLE COMPOUNDS AND USES THEREOF

CROSS-REFERENCE TO A RELATED APPLICATION

This application claims priority to European Patent Application No. 15 159 402.5, filed Mar. 17, 2015, which is incorporated herein by reference in its entirety.

FIELD OF THE INVENTION

The present invention relates to benzo-thiazolo-imidazole compounds and their uses. Moreover, the present invention relates to pharmaceutical compositions comprising such a benzo-thiazolo-imidazole compound. Furthermore, the present invention relates to the use of such a benzo-thiazolo-imidazole compound for the manipulation of cultured cells.

BACKGROUND OF THE INVENTION

Drug discovery programs for oncology typically select compounds which have a predilection for inducing cytotoxic effects in cancer cell lines versus non-cancer cells and, subsequently, for inhibiting the growth of the transplanted cancer cells in the flanks of immuno-compromised mice.

While there has been significant progress over the last decades and a number of new cancer drugs is available today, drugs for the treatment of cancer generally suffer from several problems.

One problem is that drugs for the treatment of cancer often have significant side-effects, including, for example, hair loss, problems with the fingernails and toenails, skin irritation, nausea, vomiting, fatigue, impairment of memory, concentration problems, diarrhea or constipation, anemia, swelling of limbs, lymphedema, weakening of the immune system which may result in infections, bone loss and osteoporosis, impairment of fertility, sexual side effects, incontinence, or second cancers caused by cancer treatment.

Another problem is that, despite cytotoxic effects in vitro and inhibition of tumor growth in vivo additional complications may arise because of the existence of a small subtype of cells called cancer stem cells (CSCs). Such cells are relatively resistant to therapy and are able to, after treatment with the cytotoxic drug has ended, effect repopulation with cancer cells in vivo.

The cancer stem cell hypothesis postulates that tumors are maintained by a self-renewing CSC population that is also capable of differentiating into non-self-renewing cell populations that constitute the bulk of the tumor (McDermott & Wicha). There are now numerous studies which have identified cancer stem cells in leukemia, breast cancer, brain cancer, lung cancer, colon cancer, and others (Frank et al., 2010).

To cause relapse, CSCs must have survived primary treatment. A number of factors may underlie this phenomenon, including stem cell quiescence, protected niche environment, upregulated expression of xenobiotic efflux pumps, and enhanced anti-apoptotic and DNA repair pathways.

The first identification of breast cancer stem cells was defined by the combined expression of cell surface markers $CD44^+/CD24^{-/low}/lin^-$. As few as 200 of these cells generated tumors in NOD/SCID mice whereas 20,000 cells that did not display this phenotype failed to generate tumor (Al-Hajj et al.).

Later studies suggested that aldehyde dehydrogenase 1 (ALDH-1), a detoxifying enzyme responsible for oxidation of retinol to retinoic acid, may be an even more potent marker of breast CSCs (Ginestier et al.; Morimoto et al.; Charafe-Jauffret et al.). ALDH-1-positive breast CSCs can induce tumor formation with as few as 500 cells. Breast cancer cells that expressed ALDH-1 were more likely to be estrogen receptor (ER) negative, progesterone receptor (PR) negative, and human-epidermal growth factor receptor type 2 (HER-2) positive, and frequently developed distant metastases. ALDH-1-positive cells are resistant to conventional chemotherapy with paclitaxel and epirubicin (Tanei et al.).

Previous studies have shown that adult stem cells can be identified by a side population (SP) phenotype. A SP isolated from the breast cancer cell line MCF7 was found to represent a small percentage of the total cell line and it contained the tumorigenic fraction, as demonstrated by transplantation experiments in NOD/SCID mice xenografts. This fraction was also able to reconstitute the initial heterogeneity of the cell line (Kondo et al.; Patrawala et al.).

In breast tumors, the use of neoadjuvant regimens showed that conventional chemotherapy could lead to enrichment in CSCs in treated patients as well as in xenografted mice (Li et al.; Yu et al.).

This suggests that many cancer therapies, while killing the bulk of tumor cells, may ultimately fail because they do not eliminate CSCs, which survive to regenerate new tumors.

This can be seen, e.g., from the example of breast cancer, the most common cancer in American women, and the second most leading cause of death from cancer in US women despite early detection. Approximately 30% of all patients treated for early-stage disease ultimately develop recurrence, mostly metastatic. For patients with metastatic disease at diagnosis, conventional chemotherapies are initially effective in disease control, but ultimately most patients relapse over time. Recent advances in technology have demonstrated the existence of breast cancer stem cells. These cells are currently believed to be responsible for treatment failures because of their resistance to conventional treatment.

Thus, there remains an urgent need for new pharmaceutical compounds and compositions that have less side effects and that allow to (also) effectively eradicate and target cancer stem cells. There is a need in the art for improved ways to treat cancer, such as breast cancer and leukemia. In particular, there is a need in the art for ways of treatment that have lower side effects. Moreover, there is a need in the art for improved ways to treat cancer in ways that attack a cancer at its primary site (i.e. the site of its origin) and simultaneously reduce/prevent metastasis of the cancer from its primary site to other sites. Moreover, there is a need in the art for improved ways to treat cancer in ways that specifically target cancer stem cells (such as sphere forming cells, colony forming cells, ALDH positive cells, Side Population cells, or $CD44^{HIGH}/CD24^{LOW}$ cells). Moreover, there is a need in the art for new ways to manipulate cultured cells, in particular new ways to block progression of the cell cycle and/or induce apoptosis in cultured cells.

These objects are solved by the below-described aspects of the present invention and the preferable embodiments described.

In a first aspect, the present invention relates to a benzo-thiazolo-imidazole compound having the structure represented by Formula I:

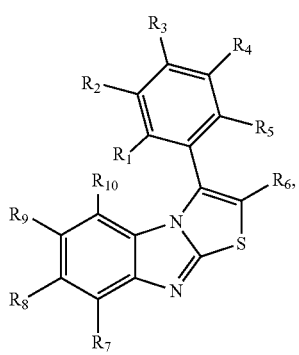

(Formula I)

wherein
R₁, R₂, R₄ and R₅ are independently selected from the group consisting of
hydrogen,
halogen (preferably F, Cl, Br, or I),
hydroxyl,
amino which is unsubstituted or substituted, preferably with one or more substituents selected from the group consisting of carbonyl, carboxyl, alkyl, alkoxy, alkenyl, cycloalkyl, aryl and heteroaryl,
nitro,
cyano,
thiol,
sulfonyl,
carbonyl, preferably an aldehyde, ketone, ester or amide,
carboxyl,
straight or branched alkyl, which is unsubstituted or substituted, preferably with one or more substituents selected from the group consisting of halogen, hydroxyl, amino, nitro, cyano, thiol, sulfonyl, carbonyl, carboxyl, alkyl, alkoxy, alkenyl, cycloalkyl, aryl and heteroaryl,
straight or branched alkoxy, which is unsubstituted or substituted, preferably with one or more substituents selected from the group consisting of halogen, hydroxyl, amino, nitro, cyano, thiol, sulfonyl, carbonyl, carboxyl, alkyl, alkoxy, alkenyl, cycloalkyl, aryl and heteroaryl,
straight or branched alkenyl, which is unsubstituted or substituted, preferably with one or more substituents selected from the group consisting of halogen, hydroxyl, amino, nitro, cyano, thiol, sulfonyl, carbonyl, carboxyl, alkyl, alkoxy, alkenyl, cycloalkyl, aryl and heteroaryl,
substituted or unsubstituted cycloalkyl, and
substituted or unsubstituted aryl or heteroaryl, preferably substituted or unsubstituted phenyl,
wherein, preferably, each of R₁, R₂, R₄ and R₅ comprises up to 18, preferably up to 14, more preferably up to 10, more preferably up to 7, more preferably up to 4, more preferably up to 3, more preferably up to 2, more preferably up to 1 carbon atoms,
wherein, more preferably, each of R₁, R₂, R₄ and R₅ is hydrogen;
R₃ is selected from the group consisting of
hydrogen,
halogen (preferably F, Cl, Br, or I),
hydroxyl,
amino which is unsubstituted or substituted, preferably with one or more substituents selected from the group consisting of carbonyl, carboxyl, alkyl, alkoxy, alkenyl, cycloalkyl, aryl and heteroaryl,
nitro,
cyano,
thiol,
sulfonyl,
carbonyl, preferably an aldehyde, ketone, ester or amide,
carboxyl,
straight or branched alkyl, which is unsubstituted or substituted, preferably with one or more substituents selected from the group consisting of halogen, hydroxyl, amino, nitro, cyano, thiol, sulfonyl, carbonyl, carboxyl, alkyl, alkoxy, alkenyl, cycloalkyl, aryl and heteroaryl,
straight or branched alkoxy, which is unsubstituted or substituted, preferably with one or more substituents selected from the group consisting of halogen, hydroxyl, amino, nitro, cyano, thiol, sulfonyl, carbonyl, carboxyl, alkyl, alkoxy, alkenyl, cycloalkyl, aryl and heteroaryl,
straight or branched alkenyl, which is unsubstituted or substituted, preferably with one or more substituents selected from the group consisting of halogen, hydroxyl, amino, nitro, cyano, thiol, sulfonyl, carbonyl, carboxyl, alkyl, alkoxy, alkenyl, cycloalkyl, aryl and heteroaryl,
substituted or unsubstituted cycloalkyl, and
substituted or unsubstituted aryl or heteroaryl, preferably substituted or unsubstituted phenyl,
wherein, preferably, R₃ comprises up to 18, preferably up to 14, more preferably up to 10, more preferably up to 7, more preferably up to 4, more preferably up to 3, more preferably up to 2, more preferably up to 1 carbon atoms,
wherein, more preferably, R₃ is methoxy or halogen, more preferably methoxy, F or Cl, more preferably methoxy;
R₆ is selected from the group consisting of
hydrogen,
halogen (preferably F, Cl, Br, or I),
hydroxyl,
amino which is unsubstituted or substituted, preferably with one or more substituents selected from the group consisting of carbonyl, carboxyl, alkyl, alkoxy, alkenyl, cycloalkyl, aryl and heteroaryl,
nitro,
cyano,
thiol,
sulfonyl,
carbonyl, preferably an aldehyde, ketone, ester or amide,
carboxyl,
straight or branched alkyl, which is unsubstituted or substituted, preferably with one or more substituents selected from the group consisting of halogen, hydroxyl, amino, nitro, cyano, thiol, sulfonyl, carbonyl, carboxyl, alkyl, alkoxy, alkenyl, cycloalkyl, aryl and heteroaryl,
straight or branched alkoxy, which is unsubstituted or substituted, preferably with one or more substituents selected from the group consisting of halogen, hydroxyl, amino, nitro, cyano, thiol, sulfonyl, carbonyl, carboxyl, alkyl, alkoxy, alkenyl, cycloalkyl, aryl and heteroaryl, straight or branched alkenyl, which is unsubstituted or substituted, preferably with one or more substituents selected from the group consisting of halogen, hydroxyl, amino, nitro, cyano, thiol, sulfonyl, carbonyl, carboxyl, alkyl, alkoxy, alkenyl, cycloalkyl, aryl and heteroaryl, substituted or unsubstituted cycloalkyl, and substituted or unsubstituted aryl or heteroaryl, preferably substituted or unsubstituted phenyl, wherein, preferably, $R_6$ comprises up to 18, preferably up to 14, more preferably up to 10, more preferably up to 7, more preferably up to 4, more preferably up to 3, more preferably up to 2, more preferably up to 1 carbon atoms, wherein, more preferably, $R_6$ is hydrogen;

$R_7$, $R_8$, $R_9$ and $R_{10}$ are independently selected from the group consisting of hydrogen, halogen (preferably F, Cl, Br, or I), hydroxyl, amino which is unsubstituted or substituted, preferably with one or more substituents selected from the group consisting of carbonyl, carboxyl, alkyl, alkoxy, alkenyl, cycloalkyl, aryl and heteroaryl, nitro, cyano, thiol, sulfonyl, carbonyl, preferably an aldehyde, ketone, ester or amide, carboxyl, straight or branched alkyl, which is unsubstituted or substituted, preferably with one or more substituents selected from the group consisting of halogen, hydroxyl, amino, nitro, cyano, thiol, sulfonyl, carbonyl, carboxyl, alkyl, alkoxy, alkenyl, cycloalkyl, aryl and heteroaryl, straight or branched alkoxy, which is unsubstituted or substituted, preferably with one or more substituents selected from the group consisting of halogen, hydroxyl, amino, nitro, cyano, thiol, sulfonyl, carbonyl, carboxyl, alkyl, alkoxy, alkenyl, cycloalkyl, aryl and heteroaryl, straight or branched alkenyl, which is unsubstituted or substituted, preferably with one or more substituents selected from the group consisting of halogen, hydroxyl, amino, nitro, cyano, thiol, sulfonyl, carbonyl, carboxyl, alkyl, alkoxy, alkenyl, cycloalkyl, aryl and heteroaryl, substituted or unsubstituted cycloalkyl, and substituted or unsubstituted aryl or heteroaryl, preferably substituted or unsubstituted phenyl, wherein, preferably, each of $R_7$, $R_8$, $R_9$ and $R_{10}$ comprises up to 18, preferably up to 14, more preferably up to 10, more preferably up to 7, more preferably up to 4, more preferably up to 3, more preferably up to 2, more preferably up to 1 carbon atoms, wherein, more preferably, each of $R_7$, $R_8$, $R_9$ and $R_{10}$ is hydrogen;

or a pharmaceutically acceptable salt thereof.

In one embodiment, said benzo-thiazolo-imidazole compound has the structure represented by Formula I:

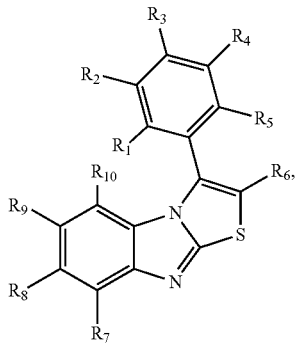

(Formula I)

wherein $R_1$, $R_2$, $R_4$ and $R_5$ are independently selected from the group consisting of hydrogen, halogen (preferably F, Cl, Br, or I), straight or branched alkyl, which is unsubstituted, wherein, each of $R_1$, $R_2$, $R_4$ and $R_5$ comprises up to 4, more preferably up to 3, more preferably up to 2, more preferably up to 1 carbon atoms, and wherein, preferably, at least two, more preferably at least three of the four groups $R_1$, $R_2$, $R_4$ and $R_5$ are hydrogen, wherein, more preferably, each of $R_1$, $R_2$, $R_4$ and $R_5$ is hydrogen;

$R_3$ is selected from the group consisting of hydrogen, halogen (preferably F, Cl, Br, or I), hydroxyl, straight or branched alkoxy, which is unsubstituted, wherein, preferably, $R_3$ comprises up to 4, more preferably up to 3, more preferably up to 2, more preferably up to 1 carbon atoms, wherein, more preferably, $R_3$ is methoxy or halogen, more preferably methoxy, F or Cl, more preferably methoxy;

$R_6$ is selected from the group consisting of hydrogen, halogen (preferably F, Cl, Br, or I), straight or branched alkyl, which is unsubstituted, wherein, preferably, $R_6$ comprises up to 4, more preferably up to 3, more preferably up to 2, more preferably up to 1 carbon atoms, wherein, more preferably, $R_6$ is hydrogen;

$R_7$, $R_8$, $R_9$ and $R_{10}$ are independently selected from the group consisting of hydrogen, halogen (preferably F, Cl, Br, or I), straight or branched alkyl, which is unsubstituted, wherein, preferably, each of $R_7$, $R_8$, $R_9$ and $R_{10}$ comprises up to 4, more preferably up to 3, more preferably up to 2, more preferably up to 1 carbon atoms, and wherein, preferably, at least two, more preferably at least three of the four groups $R_7$, $R_8$, $R_9$ and $R_{10}$ are hydrogen, wherein, more preferably, each of $R_7$, $R_8$, $R_9$ and $R_{10}$ is hydrogen;

or a pharmaceutically acceptable salt thereof.

In one embodiment, said benzo-thiazolo-imidazole compound has the structure represented by Formula II:

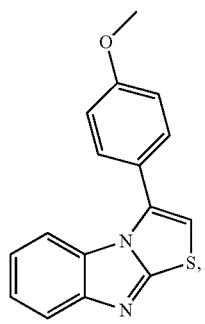
(Formula II)

or a pharmaceutically acceptable salt thereof.

In one embodiment, said benzo-thiazolo-imidazole compound or pharmaceutically acceptable salt thereof is a compound or pharmaceutically acceptable salt for use as a medicament.

In one embodiment, said benzo-thiazolo-imidazole compound or pharmaceutically acceptable salt thereof is a compound or pharmaceutically acceptable salt for use in the treatment of cancer.

In one embodiment, said cancer comprises or consists of cells that form a solid or non-solid tumor.

In one embodiment, said benzo-thiazolo-imidazole compound or pharmaceutically acceptable salt thereof is a compound or pharmaceutically acceptable salt for use in the treatment of breast cancer, colon cancer or leukemia.

In one embodiment, the cells of said cancer are characterized by a decreased expression level of the protein Numb, compared to non-cancerous cells, preferably non-cancerous cells of the same cell type, more preferably non-cancerous cells of the same cell type from the same subject, as determined by western blotting.

Preferably, said decrease in the expression level of the protein Numb is a decrease by at least 20%, preferably by at least 30%, more preferably by at least 40%, more preferably by at least 50%.

In one embodiment, said use involves the administration of said benzo-thiazolo-imidazole compound or pharmaceutically acceptable salt thereof to a patient in need thereof. In one embodiment, said patient is a mammal, preferably a human.

In one embodiment, the route of administration of said benzo-thiazolo-imidazole compound or pharmaceutically acceptable salt thereof is selected from the group consisting of intranasal administration; oral administration; inhalation administration; subcutaneous administration; transdermal administration; intradermal administration; intra-arterial administration with or without occlusion; intracranial administration; intraventricular administration; intravenous administration; buccal administration; intraperitoneal administration; intraocular administration; intramuscular administration; implantation administration; topical administration, intratumor administration and central venous administration.

In one embodiment, said compound or pharmaceutically acceptable salt is formulated for administration by a route selected from the group consisting of intranasal administration; oral administration; inhalation administration; subcutaneous administration; transdermal administration; intradermal administration; intra-arterial administration, with or without occlusion; intracranial administration; intraventricular administration; intravenous administration; buccal administration; intraperitoneal administration; intraocular administration; intramuscular administration; implantation administration; topical administration, intratumor administration and central venous administration.

In one embodiment, said benzo-thiazolo-imidazole compound or pharmaceutically acceptable salt thereof is administered by intravenous injection or by ingestion. In one embodiment, said benzo-thiazolo-imidazole compound or pharmaceutically acceptable salt thereof is formulated for administration by intravenous injection or by ingestion.

In one embodiment, said benzo-thiazolo-imidazole compound or pharmaceutically acceptable salt thereof is administered daily, preferably once every day. In one embodiment, said benzo-thiazolo-imidazole compound or pharmaceutically acceptable salt thereof is administered once every week. In one embodiment, said benzo-thiazolo-imidazole compound or pharmaceutically acceptable salt thereof is administered once every two weeks. In one embodiment, said benzo-thiazolo-imidazole compound or pharmaceutically acceptable salt thereof is administered once every four weeks. In one embodiment, said benzo-thiazolo-imidazole compound or pharmaceutically acceptable salt thereof is administered by bolus administration. In one embodiment, said benzo-thiazolo-imidazole compound or pharmaceutically acceptable salt thereof is administered for at least one week, preferably for at least two weeks, more preferably for at least one month, more preferably for at least two months, more preferably for at least three months.

In one embodiment, said benzo-thiazolo-imidazole compound or pharmaceutically acceptable salt thereof is administered to said patient at a dosage resulting in a dosage of said benzo-thiazolo-imidazole compound or pharmaceutically acceptable salt thereof in the range of from 1 to 200 mg/(kg*day), preferably in the range of from 50 to 200 mg/(kg*day).

In one embodiment, simultaneously to said administration of said benzo-thiazolo-imidazole compound or pharmaceutically acceptable salt thereof an effective amount of a chemotherapeutic agent selected from the group consisting of paclitaxel, doxyrubicin, vinblastine, vincristine, vinorelbine, topotecan, carboplatin, cisplatin, pemetrexed, irinotecan, gemcitabine, gefitinib, erlotinib, etoposide, fluorouracil, cyclophosphamide, mercaptopurine, fludarabine, ifosfamide, procarbazine and mitoxantrone is administered to said patient.

A listing of chemotherapeutic agents and the dosage to be used can be found in the 2002 Update of Recommendations for the Use of Chemotherapy and Radiotherapy Protectants: Clinical Practice Guidelines of the American Society of Clinical Oncology, J Clin Oncol. 2002 Jun. 15; 20(12):2895-903.

In one embodiment, no chemotherapeutic agent is administered simultaneously to said administration of said benzo-thiazolo-imidazole compound or pharmaceutically acceptable salt thereof. In one embodiment, no chemotherapeutic agent selected from the group consisting of paclitaxel, doxyrubicin, vinblastine, vincristine, vinorelbine, topotecan, carboplatin, cisplatin, pemetrexed, irinotecan, gemcitabine, gefitinib, erlotinib, etoposide, fluorouracil, cyclophosphamide, mercaptopurine, fludarabine, ifosfamide, procarbazine and mitoxantrone is administered to said patient simultaneously to said administration of said benzo-thiazolo-imidazole compound or pharmaceutically acceptable salt thereof.

In a second aspect, the present invention relates to a pharmaceutical composition comprising a benzo-thiazolo-imidazole compound or pharmaceutically acceptable salt thereof as defined in any of the embodiments above, and at least one pharmaceutically acceptable carrier, diluent and/or excipient.

In one embodiment, said pharmaceutical composition is a pharmaceutical composition for use as a medicament.

In one embodiment, said pharmaceutical composition is a pharmaceutical composition for use in the treatment of cancer.

In one embodiment, said pharmaceutical composition is a pharmaceutical composition for use in the treatment of breast cancer, colon cancer or leukemia.

In one embodiment, said use involves the administration of said pharmaceutical composition to a patient in need thereof.

In one embodiment, said pharmaceutical composition is administered to said patient at a dosage resulting in a dosage of said benzo-thiazolo-imidazole compound or pharmaceutically acceptable salt thereof in the range of from 1 to 200 mg/(kg*day), preferably in the range of from 50 to 200 mg/(kg*day).

In such pharmaceutical composition and the embodiments referring to it, said benzo-thiazolo-imidazole compound, said pharmaceutically acceptable salt thereof, said use, said treatment, said cancer, said administration and said patient are preferably as defined in the first aspect of the present invention or any of the embodiments referring to it.

In one embodiment, said pharmaceutically acceptable carrier or excipient comprises an ingredient selected from the group consisting of an alcohol, dimethyl sulfoxide (DMSO), physiological saline, a lipid based formulation, a liposomal formulation, a nanoparticle formulation, a micellar formulation, a water soluble formulation, a biodegradable polymer, an aqueous preparation, a hydrophobic preparation, a lipid based vehicle, and a polymer formulation.

In a third aspect, the present invention relates to the use of a benzo-thiazolo-imidazole compound or pharmaceutically acceptable salt thereof as defined in the first aspect of the present invention or any of the embodiments referring to it for the manufacture of a medicament for the treatment of cancer.

In one embodiment, said use comprises the administration of said benzo-thiazolo-imidazole compound or pharmaceutically acceptable salt thereof to a patient in need thereof.

In such use and the embodiment referring to it, said benzo-thiazolo-imidazole compound, said pharmaceutically acceptable salt thereof, said use, said treatment, said cancer, said administration and said patient are preferably as defined in the first aspect of the present invention or any of the embodiments referring to it.

In a fourth aspect, the present invention relates to a method of treatment of cancer, said method comprising the administration of a benzo-thiazolo-imidazole compound or pharmaceutically acceptable salt thereof as defined in the first aspect of the present invention or any of the embodiments referring to it or a pharmaceutical composition as defined in the second aspect of the present invention or any of the embodiments referring to it to a patient in need thereof.

Preferably, said benzo-thiazolo-imidazole compound, said pharmaceutically acceptable salt thereof, said pharmaceutical composition, said treatment, said cancer, said administration and said patient are as defined in the first aspect of the present invention, the second aspect of the present invention, or any of the embodiments referring to them.

In a fifth aspect, the present invention relates to the use of a benzo-thiazolo-imidazole compound or pharmaceutically acceptable salt thereof in a method for the manipulation of cultured cells.

As the skilled person will appreciate, such a method for the manipulation of cultured cells is a method carried out in vitro.

Preferably, said benzo-thiazolo-imidazole compound and said pharmaceutically acceptable salt thereof are as defined in the first aspect of the present invention or any of the embodiments referring to it.

Preferably, said manipulation is the induction of apoptosis and/or the induction of cell cycle arrest, preferably of cell cycle arrest in mitosis, more preferably of cell cycle arrest in early mitosis.

In one embodiment, said benzo-thiazolo-imidazole compound or pharmaceutically acceptable salt thereof is administered to said cultured cells by including it in or adding it to the culture medium used for cultivation of said cultured cells.

In one embodiment, said cultured cells are cells of a cell line.

In one embodiment, said cultured cells are mammalian cells, preferably human cells.

In one embodiment, said cultured cells are cancer cells, preferably breast cancer cells, colon cancer cells or leukemic cells.

In one embodiment, said cultured cells are cells of a cancer cell line, preferably of a breast cancer cell line, colon cancer cell line or leukemia cell line.

In one embodiment, said cultured cells are characterized by a decreased level of expression of the protein Numb compared to non-cancerous cells, preferably non-cancerous cells of the same cell type, more preferably non-cancerous cells of the same cell type from the same subject, as determined by western blotting.

Preferably, said decrease in the level of expression of the protein Numb is a decrease by at least 20%, preferably by at least 30%, more preferably by at least 40%, more preferably by at least 50%.

In one embodiment, said benzo-thiazolo-imidazole compound is applied to the cells at a concentration of 0.2 µM to 20 µM.

In one embodiment, simultaneously to said administration of said benzo-thiazolo-imidazole compound to said cultured cells, an effective amount of another agent inducing cell cycle arrest and/or apoptosis in cultured cells is administered to said cultured cells, preferably by including it in or adding it to the culture medium used for cultivation of said cultured cells.

In one embodiment, no other agent inducing cell cycle arrest and/or apoptosis in cultured cells is administered to said cultured cells simultaneously to said administration of said benzo-thiazolo-imidazole compound.

The term "substituted", as used herein, is meant to indicate that a hydrogen atom attached to a member atom within a group is replaced by another atom or group, such as replaced by halogen, hydroxyl, amino, nitro, cyano, thiol, sulfonyl, carbonyl, carboxyl, alkyl, alkoxy, alkenyl, cycloalkyl, aryl or heteroaryl; an example of a substituted alkyl is an alkyl substituted with a hydroxyl group, i.e. a hydroxy-alkyl.

The term "alkyl" refers to a monovalent straight or branched chain, saturated aliphatic hydrocarbon radical. Thus, for example, hexyl isomers are alkyls with six carbon atoms, whereas n-, iso-, sec-, and t-butyl are alkyls with four carbon atoms.

The term "alkoxy" means a group having the formula —O-alkyl, in which an alkyl group, as defined above, is attached to the parent molecule via an oxygen atom. Examples of alkoxy groups include, but are not limited to, methoxy (—O—CH$_3$ or OMe), ethoxy (—OCH$_2$CH$_3$ or —OEt), t-butoxy (—O—C(CH$_3$)$_3$ or —OtBu) and the like.

The term "alkenyl" refers to a monovalent straight or branched chain aliphatic hydrocarbon radical containing one carbon-carbon double bond. Thus, hexenyl isomers are alkenyls with six carbon atoms, whereas 1-butenyl, 2-butenyl, 3-butenyl and isobutenyl are alkenyls with four carbon atoms.

The term "cycloalkyl" refers to an unsubstituted (or, optionally, a substituted) group that comprises one or more carbocyclic ring, but that does not comprise an aromatic ring. Thus, for example, cyclohexyl is a cycloalkyl with six carbon atoms, and cyclobutyl is a cycloalkyl with four carbon atoms.

The term "halogen" refers to fluorine, chlorine, bromine, or iodine. If the halogen is a substituent, the term refers to the respective radicals.

The term "aryl" refers to an unsubstituted (or, optionally, a substituted) group that comprises one or more carbocyclic rings of which at least one is an aromatic ring. Examples for aryls are, for example, phenyl or naphthyl.

The term "phenyl", as used herein, is meant to indicate an unsubstituted (or, optionally, a substituted) phenyl group.

The term "heteroaryl", as used herein, refers to an unsubstituted (or, optionally, a substituted) group that comprises one or more carbocyclic rings of which at least one is a heteroaromatic ring, wherein the heteroaromatic ring contains from 1 to 4 (preferably 1) heteroatoms independently selected from N, O, and S. The term includes, for example, pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, thiazolyl, isothiazolyl, and thiadiazolyl, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, quinazolinyl, tetrahydroquinolinyl, tetrahydroisoquinolinyl, isoindolyl, benzodioxolyl, benzofuranyl, imidazo[1,2-a]pyridinyl, benzotriazolyl, dihydroindolyl, dihydroisoindolyl, indazolyl, indolinyl, isoindolinyl, quinoxalinyl, quinazolinyl, 2,3-dihydrobenzofuranyl, and 2,3-dihydrobenzo-1,4-dioxinyl.

The terms "KSA-101696" and "compound KSA-101696" are used interchangeably and refer to a compound with the structure shown in FIG. 8.

The compounds of formula I in accordance with the present invention may be produced by a method wherein

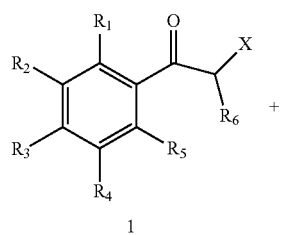

1

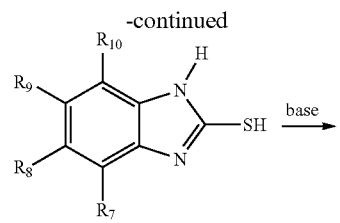

2

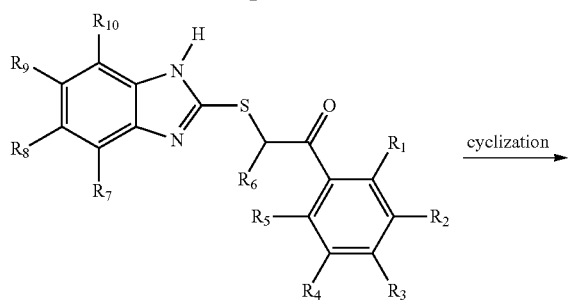

3

Formula I

The compounds of Formula I were prepared by the reaction of halo ketones 1 (X=halogen) with benzimidazoles 2 in the presence of a base such as potassium hydroxide in EtOH/H$_2$O or triethyl amine in EtOH to give sulphides 3. Cyclization of the latter sulphides afforded the corresponding compounds of Formula I.

"Cancer" as used herein, refers to a diseases caused by the uncontrolled, abnormal growth of cells that can spread to adjoining tissues or other parts of the body. Cancer cells can form a solid tumor, in which the cancer cells are massed together, or exist as dispersed cells, as in leukemia.

The terms "cancer cell" and "cancerous cell" are used interchangeably and refer to a cell characterized by uncontrolled, abnormal growth and the ability to invade another tissue or a cell derived from such a cell. Cancer cell includes, for example, a primary cancer cell obtained from a patient with cancer or cell of a cell line derived from such a primary cancer cell. Examples of cancer cells include, but are not limited to, breast cancer cells, cells of a breast cancer cell line, colon cancer cells, cells of a colon cancer cell line, cancer stem cells, and hematological cancer cells such as cells of myelomas, leukemic cells or lymphoma cells.

"Leukemia" as used herein, refers to a disease involving the progressive proliferation of abnormal leukocytes found in hemopoietic tissues, other organs and in the blood, resulting in increased numbers of leukocytes. "Leukemic cells" refers to leukocytes characterized by an increased abnormal proliferation of cells. Leukemic cells may be obtained from a subject diagnosed with leukemia. The term includes, but is not limited to, acute lymphocytic leukemia (ALL), acute myelogenous leukemia (AML) and chronic myelogenous leukemia (CML), and monocytic leukemia.

"Cancer stem cell", abbreviated "CSC", refers to a cell that is capable of self-renewal and differentiating into the lineages of cancer cells that comprise a tumor or hematological malignancy. Cancer stem cells are uniquely able to initiate and sustain the disease. Tumors are maintained by a self-renewing cancer stem cell population that is also capable of differentiating into non-self-renewing cell populations that constitute the bulk of the tumor (McDermott & Wicha). Cancer stem cells have for example been identified in leukemia, breast cancer, brain cancer, lung cancer, colon cancer, and others (Frank et al., 2010) Cancer stem cells include sphere forming cancer cells, colony forming cancer cells, cells defined by the combined expression of cell surface markers CD44$^+$/CD24$^{-/low}$/lin$^-$ (Al-Hajj et al.), cancer cells positive for the marker aldehyde dehydrogenase 1 (ALDH-1) (Ginestier et al.; Morimoto et al.; Charafe-Jauffret et al.), and side population (SP) cells (Kondo et al.; Patrawala et al.). In breast tumors, the use of neoadjuvant regimens showed that conventional chemotherapy could lead to enrichment in CSCs in treated patients as well as in xenografted mice (Li et al.; Yu et al.).

A "sphere forming cancer cell" is a cancer cell with stem cell properties in which that cells can grow and form spheres in serum-free medium in an ultra-low attachment plate.

A "colony forming cancer cell" is a cancer cell with stem cell properties that can grow from a single cell to form a colony. Such cells may be obtained by culturing cells at low density, e.g. 5000 cells per 60 mm dish plate.

A "CD44$^+$/CD24$^{-/low}$" cell" is a cancer cells with stem cell properties in which cells are highly expressing cell surface marker CD44 and weakly expressing cell surface marker CD24. Such cells may be isolated from a cancer cell line or primary tumor with a Flow Cytometric cell sorter.

An "ALDH-1 positive cell" is a cancer cells with stem cell properties which expresses Aldehyde dehydrogenases-1 enzyme. Such cells may be isolated from a cancer cell line or primary tumor sample with a Flow Cytometric cell sorter using the ALDEFLUOR™ kit.

A "side population cell" is a cancer cell with stem cell properties which is able to efflux the fluorescent DNA-binding dye (Vybrant® DyeCycle™). Such cells may be isolated from a cancer cell line or primary tumor with a Flow Cytometric cell sorter.

The term "treatment", as used herein, refers to the process of providing a subject with a pharmaceutical treatment, e.g., the administration of a drug, such that a disease or disease state is alleviated, reduced, minimized, halted or even healed, and/or such that the chances of a relapse into the disease state are reduced or a relapse into the disease state is even prevented.

"Pharmaceutically acceptable", as used herein for example in the context of a pharmaceutically acceptable salt of a compound, refers to a substance (or composition) that is non-toxic to the subject to which it is administered and that thus can be used in the formulation of a pharmaceutical product. If the pharmaceutically acceptable substance is part of a pharmaceutical composition, then the term also implies that the pharmaceutically acceptable substance is compatible with the other ingredients of the said pharmaceutical composition.

Examples of pharmaceutically acceptable salts are addition salts which include, without limitation, the non-toxic inorganic and organic acid addition salts such as the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enantate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the nitrate derived from nitric acid, the perchlorate derived from perchloric acid, the phosphate derived from phosphoric acid, the phthalate derived from phthalic acid, the salicylate derived from salicylic acid, the sorbate derived from sorbic acid, the stearate derived from stearic acid, the succinate derived from succinic acid, the tartrate derived from tartaric acid the sulphate derived from sulphuric acid, the tartrate derived from tartaric acid, the toluene-p-sulphonate derived from p-toluene sulphonic acid, the naphthaline-1,5-disulphonate derived from naphthaline-1,5-disulphonic acid and the like. Such salts may be formed by procedures well known and described in the art.

While the compound according to the present invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries. As the skilled person will appreciate, the ingredients of such a pharmaceutical composition must be compatible with the other ingredients of the formulation and not harmful to the recipient thereof.

The term "pharmaceutically acceptable carrier, diluent and/or excipient" refers to a non-toxic, inert, solid, semi-solid, or liquid diluent material or formulation auxiliary of any type. "Pharmaceutically acceptable" in this context is meant to designate that said carrier is compatible with the other ingredients of the pharmaceutical composition and not harmful to the patient that the pharmaceutical composition is administered to. Examples of pharmaceutically acceptable carriers include, but are not limited to, water, water-propylene glycol solutions, or aqueous polyethylene glycol solutions.

The production of medicaments or pharmaceutical compositions containing a benzo-thiazolo-imidazole compound according to the present invention or a pharmaceutically acceptable salt thereof and their application can be performed according to well-known pharmaceutical methods.

A medicament of the invention may be a medicament suitable for oral, rectal, bronchial, nasal, topical, buccal, sub-lingual, transdermal, parenteral (including cutaneous, subcutaneous, intramuscular, intraperitoneal, intravenous, intraarterial, intracerebral, intraocular injection or infusion) administration, or a medicament in a form suitable for administration by inhalation or insufflation, including powders and liquid aerosol administration.

Further details on techniques for formulation and administration may be found in the latest edition of Remington's Pharmaceutical Sciences (Maack Publishing Co. Easton, Pa.). The term "effective amount", as used herein, refers to an amount that produces a desired treatment effect in a subject. This amount will vary depending upon a variety of factors, including, but not limited to, the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. A person skilled in the art will be able to determine an effective amount through routine experimentation, namely by monitoring a subject's response to administration of a compound and adjusting the dosage accordingly. For additional guidance, see Remington: The Science and Practice of Pharmacy 20th Edition, Gennaro, Ed., Williams & Wilkins Pennsylvania, 2000.

At some instances, the present application indicates that "simultaneously to" administration of a first agent a second agent is administered. This is meant to designate that the second agent is administered (a) at the same time at which said first agent is applied to the patient, (b) at a time that lies between individual administrations of said first agent, if administration of first agent occurs in several individual administrations, or (c) after administration of said first agent, while the administered first agent is still present in the tissue, blood, or digestive system of the patient or on the surface of the skin of the patient.

"Cultured cells", as used herein, refers to cells growing under conditions of in vitro culture. Thus cultured cells are free tissue cells that are cultivated in a system entirely apart from their normal environment in which the conditions and factors for growth can be varied at will within the boundaries tolerated by the cells.

As used herein, the term "in vitro" means occurring outside of a living organism. The term in vitro can describe processes/conditions occurring within a cell culture system. In contrast to "in vitro", the term "in vivo" means occurring within a living organism.

When the present application refers to the "manipulation of cultured cells", as used herein for example in the context of a certain compound being used in a method for the "manipulation of cultured cells", this refers to a situation where desired changes are brought about in said cultured cells or their molecular components, typically by applying an effective amount of said compound into contact with said cultured cells and allowing the compound to act on said cultured cells for a time span sufficient to bring about such effects. Manipulations of cultured cells include, for example, inducing cell cycle arrest or inducing apoptosis in said cultured cells.

The present inventors have surprisingly found that the benzo-thiazolo-imidazole compounds according to the present invention, such as the compound with the structure represented in FIG. 8 (referred to also as KSA-101696 in this application), have effects in the treatment of cancer, in particular in the treatment of breast cancer, colon cancer and leukemia. The present inventors have moreover found that, surprisingly, the compounds of this group also have effects on cultured cells, and are for example capable of causing cell cycle arrest of cultured cells in early mitosis and the induction of apoptosis.

Moreover, surprisingly KSA-101696 showed even higher effectiveness on cancer cells with aggressive behavior such as chemoresistance and metastasis than on chemosensitive and non-metastasized (non-aggressive) cancer cells.

Without wishing to be bound by theory, it seems possible that one mechanism how KSA-101696 may affect cells may be by increasing the expression of Numb protein, which is the natural blocker of the Notch pathway.

The Numb protein regulates the Notch-, Hedgehog- and TP53-activated pathways, endocytosis (it is involved in cargo internalization and recycling), determination of polarity (it interacts with the PAR complex, and regulates adherens junctions and tight junctions), and ubiquitination (it exploits this mechanism to regulate protein function and stability). This complex biochemical network lies at the heart of Numb's involvement in diverse cellular phenotypes, including cell fate developmental decisions, maintenance of stem cell compartments, regulation of cell polarity and adhesion, and migration and induced differentiation for therapeutics purposes in humans and animals.

Numb functions as an intrinsic cell fate determinant that is asymmetrically localized in neuronal precursor cells where it influences cell fate by antagonizing signaling from the Notch receptor. Decreased Numb has been demonstrated in mammary carcinomas and higher percentage of the tumors with deficient or reduced expression belonged to the triple-negative (ER−/PR−/HER2−) subgroup (ER: estrogen receptor; PR: progesterone receptor; HER2: human epidermal growth factor receptor 2) compared to tumors with retained Numb expression. Furthermore, decreased expression was associated with poorer distant disease-free survival.

Notch is a fundamental signaling pathway that regulates embryonic cell fate specification. Its driven tumorigenesis in human breast cancer has been suggested by the development of adenocarcinomas in the murine mammary gland following pathway activation and the loss of Numb expression, in a large proportion of breast carcinomas. Furthermore, during pathway activation, Notch intracellular domain (NICD) translocates to the nucleus and binds the CSL ("CBF-1, Suppressor of Hairless, Lag-2") transcription factor. The NICD/CSL complex induces expression of target genes, including those of the hairy/enhancer of split (Hes) family, the cell cycle regulator p21 and cyclin D1. Cancer stem cells are dependent on a number of key signaling pathways. One of these is the Notch pathway. For example, in breast cancer, it has been reported that the fate of CSCs is controlled by the Notch pathway through induction of Jagged-1. More importantly, self-renewal capacity of mammospheres is enhanced 10-fold when cultured in the presence of a synthetic peptide derived from the DSL (delta-Serrate-Lag2) domain, which is highly conserved in all Notch ligands and capable of Notch receptor activation. On the other hand, the self-renewal capacity was inhibited by Notch 4 blocking antibody or an inhibitor of the γ-secretase enzyme.

BRIEF DESCRIPTION OF THE FIGURES

In the following, reference is made to the figures, wherein:

FIGS. 9A-9B show data obtained by quantification of western blots (FIG. 9A) and data obtained by flow cytometry and western blotting (FIG. 9B) to examine the ability of KSA-101696 to induce apoptosis in different breast cancer cell lines.

EXAMPLES

Figure 1A:
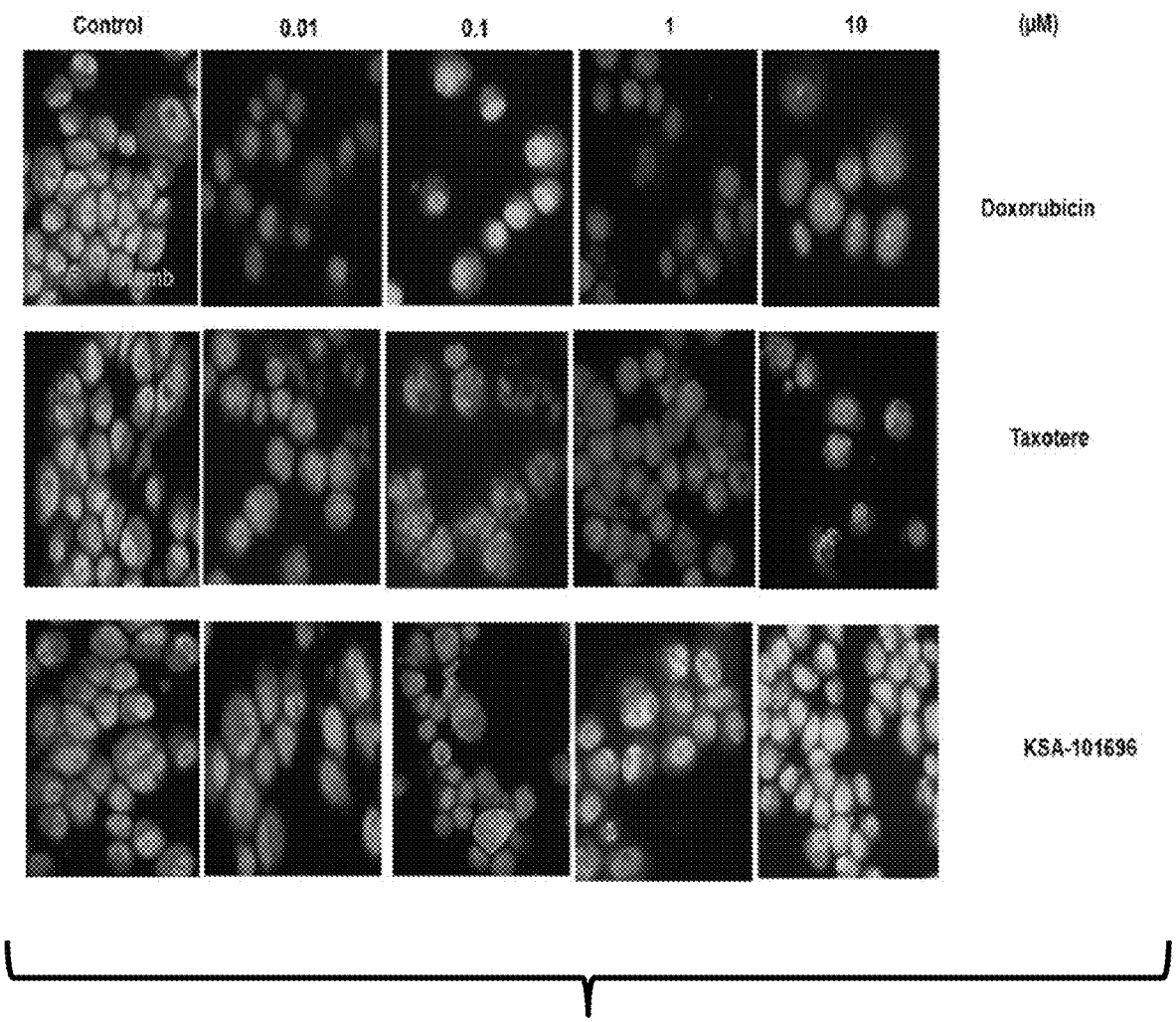
FIGS. 1A-1C show data from immunofluorescence experiments studying the effects of K101696 on the protein levels of Numb and cleaved Notch.

In the following, reference is made to the examples, which are given to illustrate, not to limit the present invention.

Example 1

Cell Line and Tissue Culture

SKBR3, MCF-7, MDA-MB-468, MDA-MB-231 and BT-474 breast cancer cell lines were purchased from the American Type Culture Collection. SKBR-3 cells were cultured in McCoy's 5A (GIBCO), and other cell lines cultured in DMEM (Dulbecco's modified Eagle's medium). The media supplemented with 10% FBS (fetal bovine serum; Cambrex Bio Science), 100 IU/mL penicillin and 100 mg/mL streptomycin. Cell viability was assessed by trypan blue exclusion analysis. Cell numbers were determined by using a hemocytometer.

Cell Proliferation by $^3$H-Thymidine Uptake Assay

In vitro antitumor activity of the compound was assessed by $^3$H-thymidine uptake. The cells were treated and they were about 60% confluent. Cells were seeded at $4\times10^3$ cells per well in a 96 well plate in DMEM containing 10% FBS for 24 h followed by treatment with control media (0.1% DMSO) or media containing different concentration of the compound incubated for 72 h at 37° C. in 5% $CO_2$. Cells were labelled by addition of $^3$H-thymidine (Amersham, Chiltern Hills, London, UK) at 1 µCi/well for 18 h before harvesting. $^3$H-thymidine uptake was measured using a 1450 Micro Beta PLUS liquid scintillation counter (Wallac, Waltham, Mass., USA).

Flow Cytometric Analysis of Cellular DNA Content $2\times10^6$ cells were fixed in 1 ml ethanol (70%) for 60 min at room temperature. Harvested cells were resuspended in 1 ml Na citrate (50 mM) containing 250 µg RNase A and incubated at 50° C. for 60 min. Next, cells were resuspended in the same buffer containing 4 µg propidium iodide (PI) and incubated for 30 min before being analyzed by flow cytometry (Becton Dickinson, San. Jose, Calif., USA). The percentage of cells in various cell cycle phases was determined by using Cell Quest Pro software (Becton Dickinson).

Measurement of Annexin V Binding by Flow Cytometry

It is known that loss of phospholipid asymmetry of the plasma membrane is an early event of apoptosis. The annexin V binds to negatively charged phospholipids, like phosphatidylserine. During apoptosis, the cells react to annexin V once chromatin condenses but before the plasma membrane loses its ability to exclude propidium iodide (PI). Hence, by staining cells with a combination of fluorescein isothiocyanate (FITC), annexin V and PI it is possible to detect non-apoptotic live cells, early apoptotic cells and late apoptotic or necrotic cells.

Annexin-V staining was performed by using Vybrant Apoptosis Assay Kit #2 (Molecular Probes) following the manufacturer's recommendations. Annexin-V stained cells were analyzed by flow cytometry, measuring the fluorescence emission between 515 nm to 545 nm.

Cancer Stem Cell Sorting

MDA-MB-468 Cells harvested, washed and incubated in aldefluor assay buffer containing an ALDH substrate (BAAA (BODIPY®-aminoacetaldehyde). For negative control, half of the cells of each sample was removed to another FACS tube and incubated under identical condition with DEAB, a specific inhibitor of ALDH enzyme. Then the cells were stained with the following directly conjugated monoclonal antibodies anti-mouse CD44-APC-Cy7 (Biolegend), anti-mouse CD24-Pacific Blue (EXBIO Praha, a.s.). All analyses and cell sorting were performed on a FACSAria™ cell sorter (BD Biosciences). Debris and cell clusters were excluded during side-scatter and forward-scatter analyses.

Mammosphere Formation Assay

Cell were harvested and counted by using trypan blue to exclude the dead cells. Cells cultured in suspension (1000 cells/100 µL) in serum-free mammary epithelium basal medium, supplemented with B27 supplement 1:50; (GIBCO), 20 ng/mL EGF (epidermal growth factor; Preprotech), 5 µg/mL insulin (Sigma), 1% Antibiotic-Antimycotic (GIBCO) and 0.5 µg/ml hydrocortisone (Sigma), as described previously (Dontu et al.). Mammospheres were allowed to grow for 7 days, then treated for 72 h by either control media (0.1% DMSO) or media containing different concentrations of the compound. Mammospheres were counted on a Leitz Labovert inverted Microscope. Mammosphere size was measured and a picture was taken on a Evos transmitted light microscope.

Aldofluor Assay

SKBr3 cells with or without treatment harvested, washed and incubated in aldefluor assay buffer containing an ALDH substrate (BAAA). For negative control, half of the cells of each sample was removed to another FACS tube and incubated under identical condition with DEAB (diethylaminobenzaldehyde), a specific inhibitor of ALDH enzyme.

2-D Colony Formation Assay

Cells were treated with different concentration of the compound or control medium containing 0.1% DMSO for 72 h. Cells were harvested and counted by using trypan blue to exclude the dead cells. A 5000 viable cells of treated and control cells were suspended in 3 ml DMEM supplemented with 10% FBS (Cambrex Bio Science) and seeded in a 60 mm tissue culture dish (Falcon, BD). The next day, a new fresh media was added and the cells were allowed to grow forming colonies for 14 d. The cells were then stained with methylene blue (Sigma-Aldrich, St. Louis, Mo., USA) and colonies containing more than 20 cells were counted.

Migration and Invasion Assay

Figure 6A:
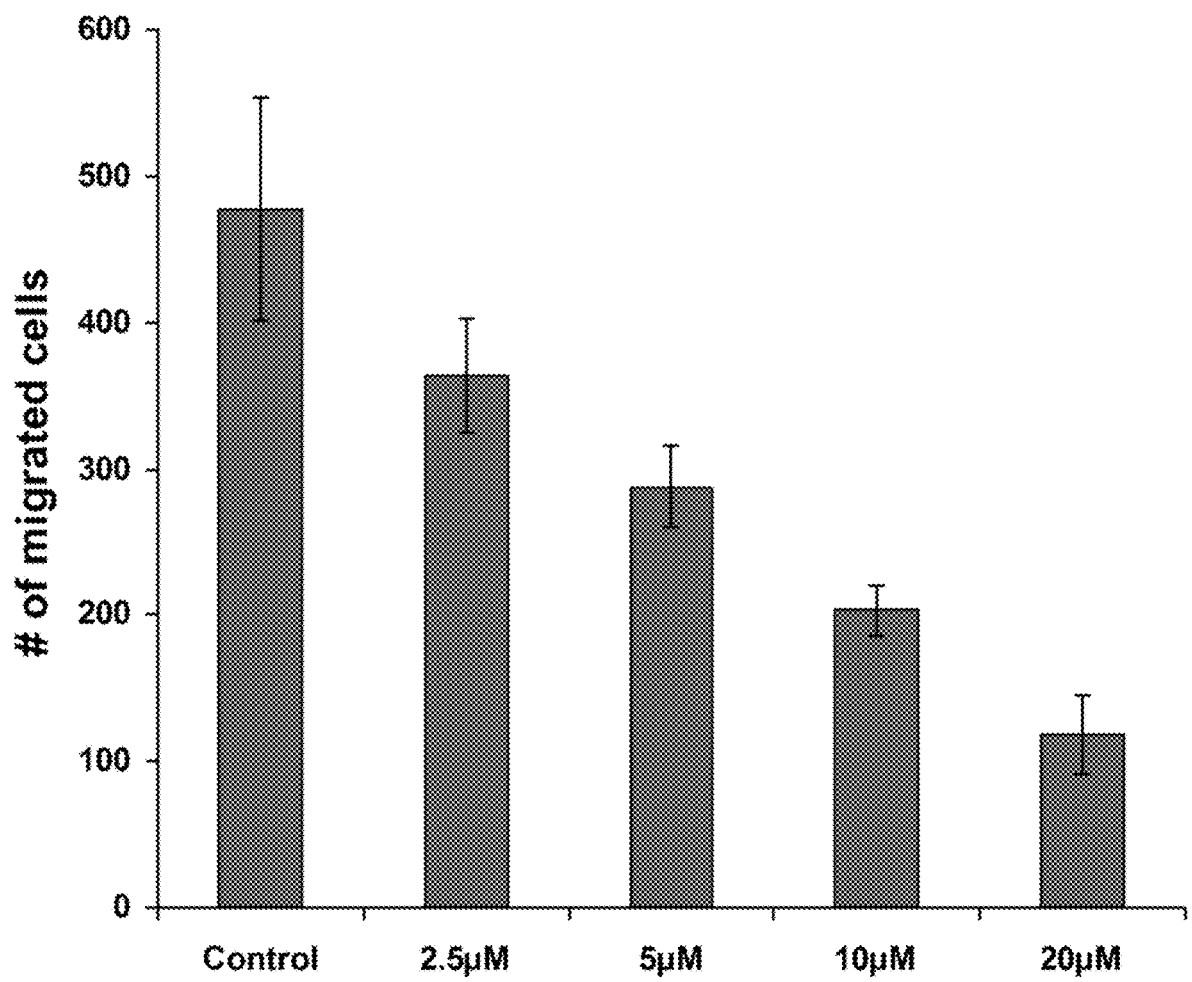
FIGS. 6A-6B show experimental data to study the effects of KSA101696 in a cell migration assay (FIG. 6A) and a cell invasion assay (FIG. 6B).
Figure 6B:
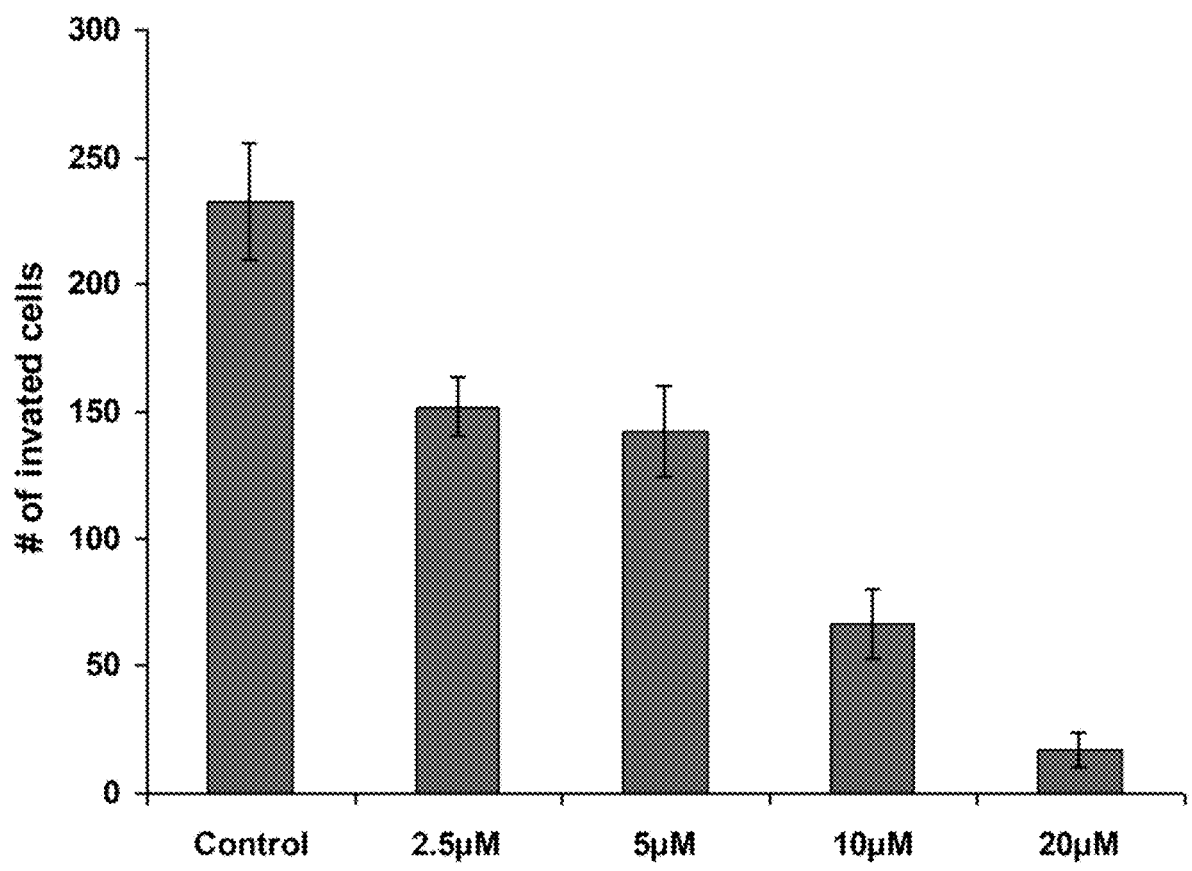

To assess the metastatic potential of tumor cells, their migration and invasion was evaluated using the 24-well BD BioCoat Matrigel Invasion Chamber as per the manufacturer guideline (BD Bioscience). In brief, 750 μl of migration buffer (serum-free media with or without treatment) or chemoattractants (serum-containing media) were added to the lower wells. Cells were washed three times in migration media and 500 μl ($1$-$2 \times 10^5$) of cells were added to the upper wells separated by an 8 micron pore size PET membrane with a thin layer of matrigel basement membrane matrix (for invasion) or without (for migration). The membranes were stained with Diff Quick stain (Fisher Scientific) after removing the non-migrated cells from the top of the membrane with Q-tips. After air drying, the membranes were cut and mounted on slides with oil and cells that had migrated to the underside of the filter were counted using a light microscope (Zeiss Axio Observer) in five randomly selected fields (magnification: 40×). Each assay was performed in triplicate and repeated at least five times. The results were expressed as mean±SD of migrating cells per field counted (FIGS. 6A-6B).

Antitumor Activity in Mice

Nude mice (Jackson Laboratories, Bar Harbor, Me., USA) were injected with $4 \times 10^6$ cells of MDA-MB-468 in the mammary pad and tumor size was measured weekly using a caliper. When the tumor reached approximately 100 mm$^3$ diameter the mice were divided into a control group and a group treated with KSA-101696 200 mg/kg via intraperitoneal injection (three cycles every four days). Apparent toxicity as determined by body weight loss is recorded by measuring total body weight. Breeding, care and sacrifice of the animals were carried out in accordance with the protocols approved by the Animal Care and Use Committee of the King Faisal Specialist Hospital and Research Centre.

Western Blotting

SDS-PAGE was performed using 12% separating minigels. Equal amounts of protein extract (30 μg) from different samples were placed in boiling water for 2 min in the presence of SDS gel sample buffer (0.5 M Tris pH 6.8, 10% glycerol, 10% SDS, 5% 2-mercaptoethanol, 1% bromophenol) and electrophoresed for 2 h at 75 V. After transfer onto polyvinylidene difluoride membrane (PVDF), the membrane was incubated overnight with the appropriate antibodies (GADPH and p-Numb antibodies were purchased from Cell Signaling). Visualization of the second antibody was performed using a chemiluminescence detection procedure according to the manufacturer's protocol (Amersham Pharmacia Biotech).

Determination of LD$_{50}$ Value

Swiss Webster Albino mice were housed in groups of 2 or 4 in elevated steel wire-mesh cages in a controlled room maintained at a temperature of 22±2° C., relative humidity of 50±10% and a 12 h light-dark cycle. Rodent diet chow (feed) provided by Grain Silos Flour Mills Organization, Riyadh, Saudi Arabia, and tap water for drinking were made available ad lib.

Male mice were divided into various groups (n=10 animals per group). Each group was administered a different dose of the respective compound via the intraperitoneal (i.p.) route. The dose range used was 100-5000 mg/kg. Each group of animals was administered a single does and observed continuously for the first 2 h, then every hour for 6 h and thereafter at 24, 48 and 72 hours following the administration of the compound KSA-101696 or Doxorubicin, respectively.

During the observation periods there was a continuous record of any behavioral changes and clinical symptoms that caused by effects on the central and autonomic nervous systems, the respiratory and the cardiovascular systems or any other action on the gastrointestinal tract, the renal systems, eye, skin, skeletal muscles etc.

During the 72 hour observation period the number of animals that died in every group was recorded. The percentage of death calculated and converted to probits to calculate the LD$_{50}$ value for each compound in mg/kg. The LD$_{50}$ value reported in this study provided compounds in their liquid form in the provided concentrations.

Example 2

Unless indicated otherwise, all methods mentioned in this example were carried out as described in Example 1.

MDA-MB-231 breast cancer cells were treated either with vehicle (control) or with 0.01 μM, 0.1 μM, 1 μM or 10 μM final concentration of doxorubicin, taxotere or KSA-101696. Then, the cells were cytospun to glass slides by centrifugation at 800 rpm for 3 min. Slides were then air-dried overnight and 4% formaldehyde fixed for 10 min. For staining, the cell membrane was permeabilized with 0.5% triton-X (Sigma) followed by overnight incubation with primary antibodies (anti-Numb, Abcam) and (anti-intracellular Notch-1, Cell Signalling) at 1:100. Cells were washed and stained with AlexaFluor goat anti-rabbit IgG 488 (Invitrogenat) 1:400 for 30 minutes. 300 nM DAPI (Invitrogen, Carlsbad, Calif., USA) was added for 10 minutes to counterstain the nuclei. Slides were mounted and immunofluorescence was visualized using BD Pathway 855 microscope.

Figure 1B:
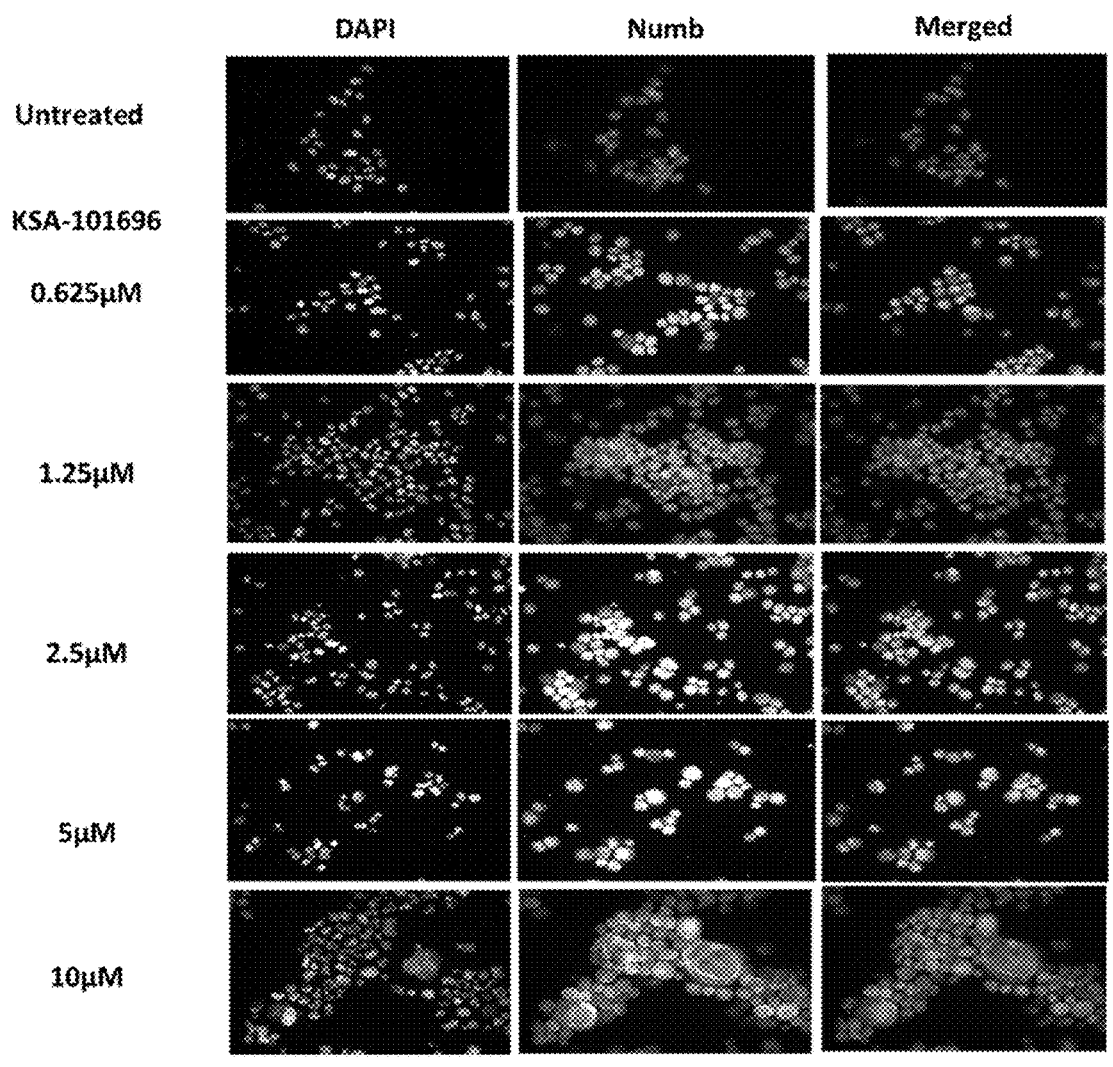
Figure 1C:
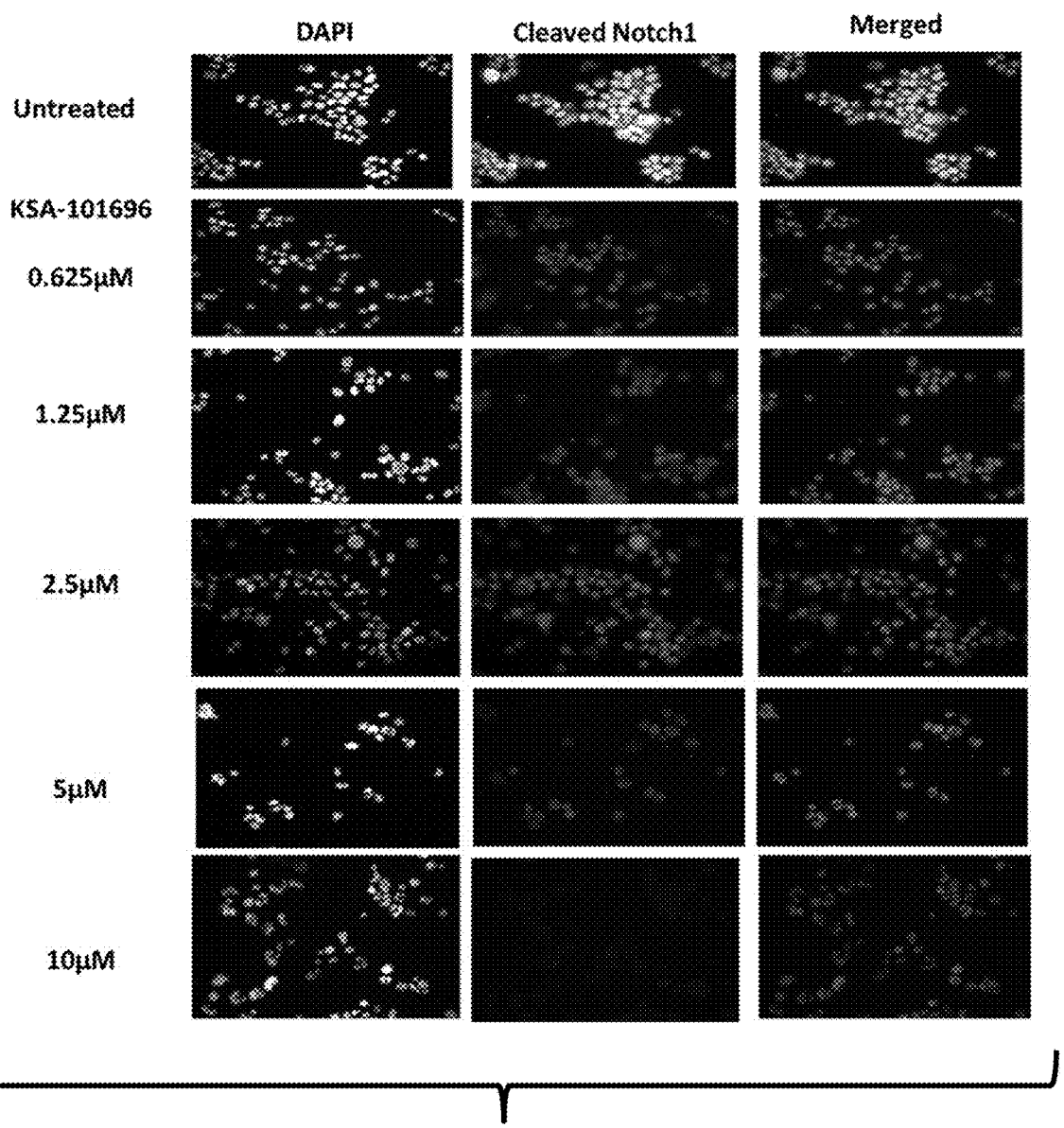
Figure 8:
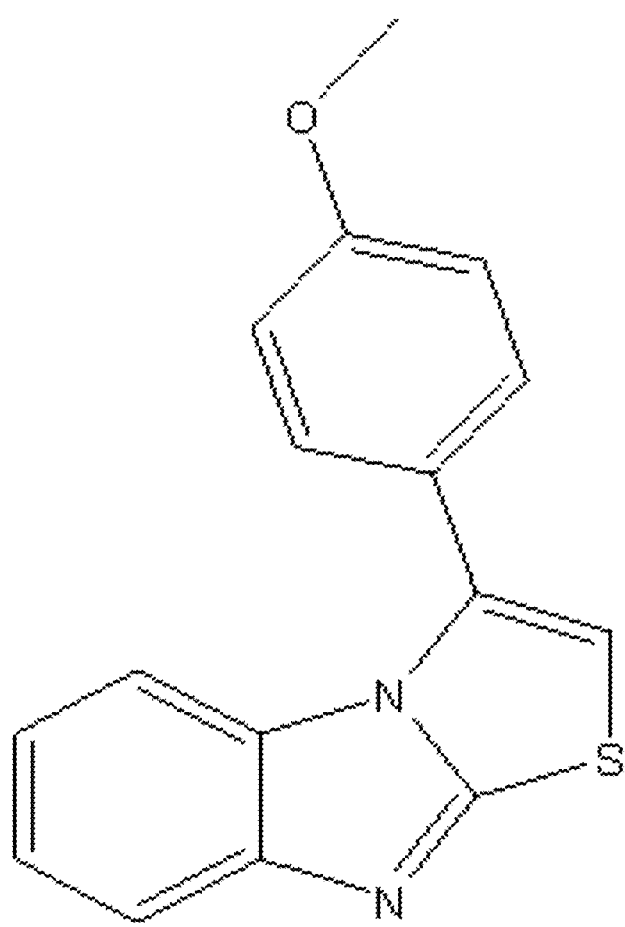
FIG. 8 shows the structure of compound KSA-101696 (3-(4-methoxyphenyl)benzo[4,5]imidazo[2,1-b]thiazole).

Numb exerts its functional role on cell fate decisions by antagonizing Notch signaling activities. The molecular mechanisms underlying this relationship appear to rely on the ubiquitination of the membrane bound Notch-1 receptor and the subsequent degradation of its NICD (Notch intracellular domain) following receptor activation. By using immunofluorescence microscopy, the treatment of MDA-MB-231 breast cancer cells by KSA-101696 (for structure of KSA-101696, see FIG. 8) induced Numb while the chemotherapeutic agents doxorubicin and taxotere inhibited Numb expression and subsequently activated the Notch self-renewal pathway. More importantly, KSA-101696 is a selective and highly potent inhibitor of intracellular Notch-1 by activating the expression of cell fate determinant Numb, in sub-micromolar concentration (0.625 μM) as shown in FIGS. 1B and 1C.

In another experiment, the in vitro antitumor activity of the compound was assessed by a 3H-thymidine uptake experiment. To this end, cells of the tumor cell lines MCF-7, SKBR3 and MDA-MB-468 were seeded at $4 \times 10^3$ cells per well in a 96 well plate in DMEM containing 10% FBS for 24 h followed by treatment with control media (0.1% DMSO) or media containing different concentration of the compound (5 μM, 10 μM, 20 μM, 40 μM or 80 μM final concentration of KSA-101696) and incubated for 72 h at 37° C. in 5% CO$_2$. At about 60% confluency, cells were labelled by addition of 3H-thymidine (Amersham, Chiltern Hills, London, UK) at 1 μCi/well for 18 h before harvesting. 3H-thymidine uptake was measured using a 1450 Micro Beta PLUS liquid scintillation counter (Wallac, Waltham, Mass., USA).

Figure 2A:
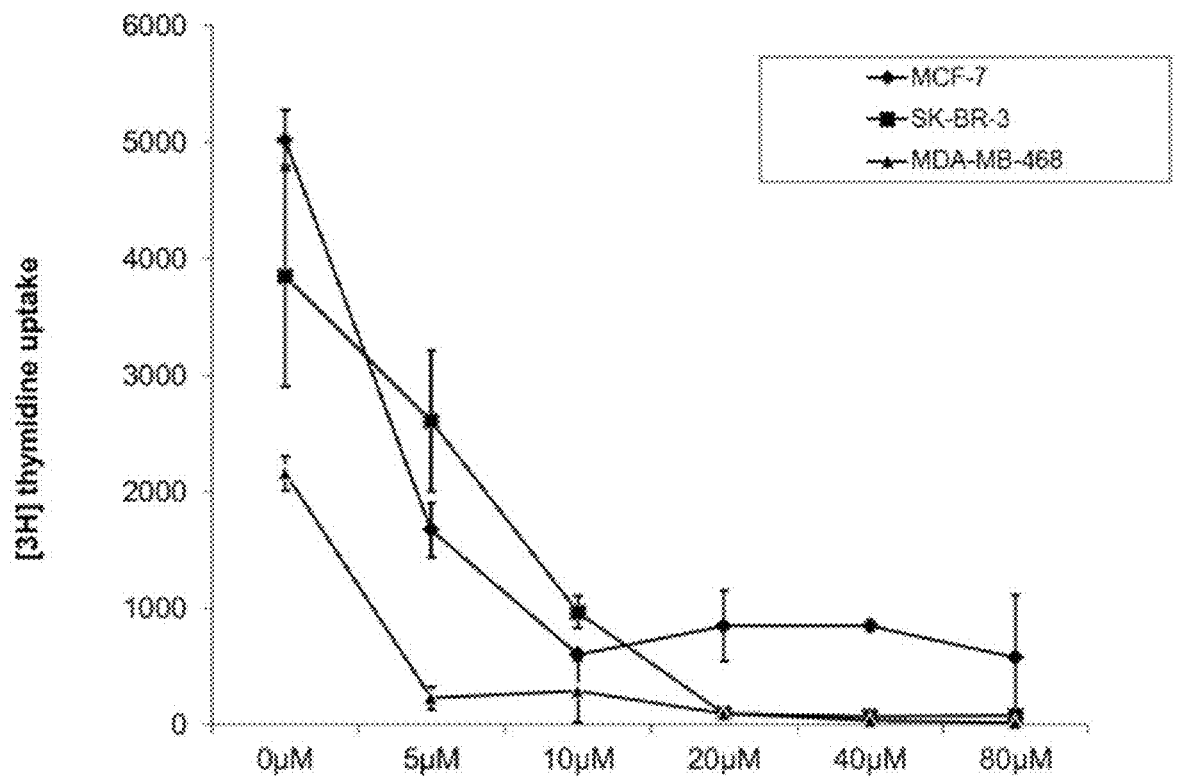
FIGS. 2A-2D show experimental data from $^3$H-thymidine uptake experiments examining the effects of KSA-101696 on the growth of tumor cell lines (FIG. 2A), data from a flow cytometric analysis of cellular DNA content to study the effects of KSA-101696 on progression of the cell cycle (FIG. 2B), and data from a flow cytometric analysis after Annexin-V staining to examine if KSA-101696 induces apoptosis in different cell lines (FIGS. 2C-2D).

As can be seen in FIG. 2A, the compound inhibited the growth of tumor cell lines MCF-7, SKBR3 and MDA-MB-468 in a dose-dependent manner. The selection of these cell lines was dependent on the phenotypical and molecular bases. The $IC_{50}$ dose on MDA-MB-468 was about 2.5 µM, for MCF-7 about 5 µM and the highest does on SKBR3 cells with $IC_{50}$ of 7.5 µM. The small difference in $IC_{50}$ does between the tested cell lines demonstrated that the cell proliferation inhibition activity of the compound is not dependent of either the estrogen receptor (ER) expression nor human-epidermal growth factor receptor type 2 (HER-2) positivity or ER-PR-HER2-negative status.

Figure 2B:
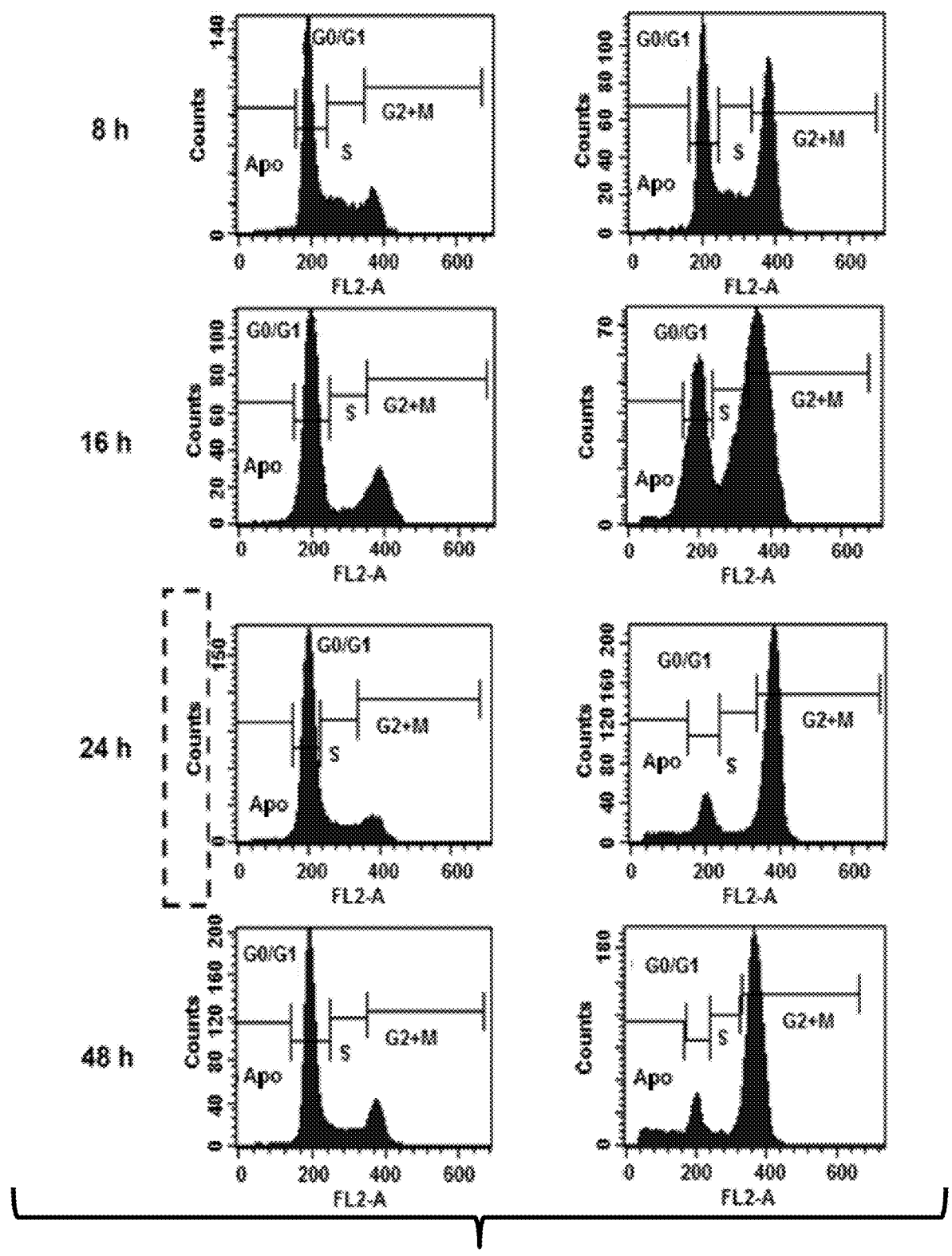

To gain insight into the mechanism by which anti-proliferation was achieved, the effect on cell cycle distribution was investigated by fluorescence-activated cell sorting (FACS) analysis. MCF-7 cells were exposed to 20 µM of the compound KSA-101696 for 8, 16, 12 and 48 h, which resulted in accumulation of cells in G2/M phase in a time-dependent manner (see FIG. 2B). This was also accompanied by a compensatory decrease in G1 phase cells. Based on histograms the compound blocks the cells on early stage of mitosis, thereby inhibiting the transition of the cells to complete mitosis.

Apoptotic cell death plays a critical role in normal cell development, tissue homeostasis, and the regulation of the immune system. Inadequate apoptosis is an integral part of cancer development. For anticancer drug therapy, it is critical that those cells with the highest tumorigenic potential are killed, while the drug is tolerated well by surrounding normal tissues. Many of side effects of chemotherapeutic agents are as a result of lack of killing selectivity toward cancer cells rather than normal cells, especially those cells with high proliferative nature. Therefore, two key questions were addressed. Firstly, is the compound induced apoptosis in cancer cells and not in normal cells? And secondly, is the apoptosis induction is selectively to those cells with stem cell characters.

Figure 2C:
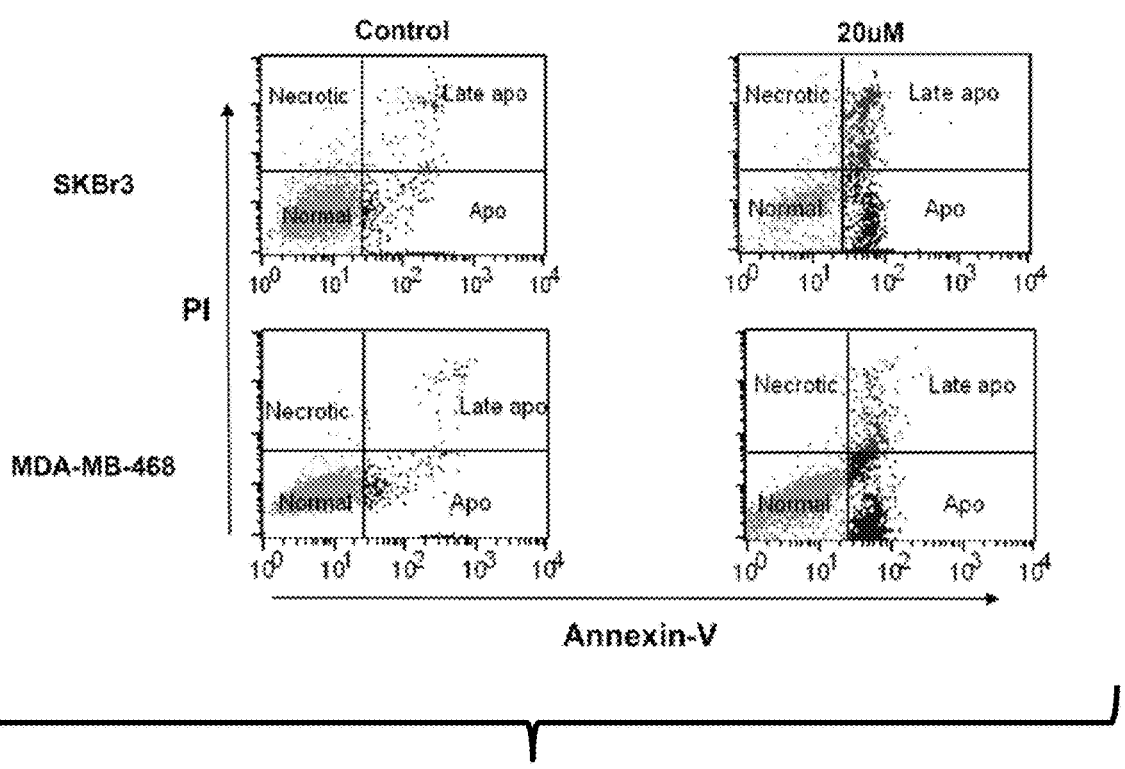
Figure 2D:
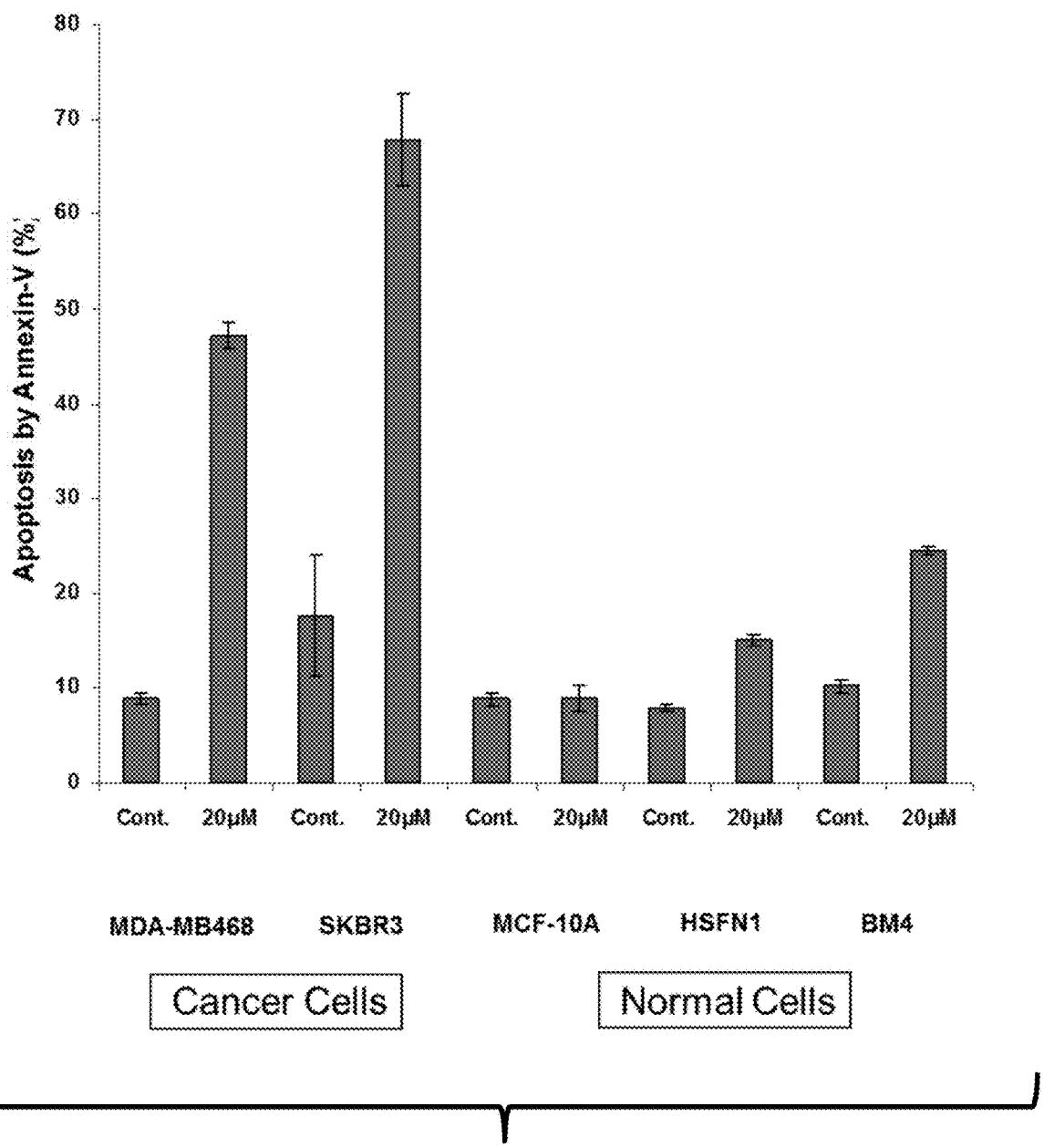

To evaluate the selective-apoptotic effect of the compound in cancer cells but not normal cells, the cancer cell lines SKBR3, MDA-MB-468, and normal cells MCF-10 A, HSFN1 (human foreskin cells) and BM4 (bone marrow derived mesenchymal stem cells) were used. KSA-101696 induced apoptosis in cancer cell lines MDA-MB-468 and SKBR-3. On the other hand, KSA-101696 induced little apoptotic effect on normal cells, which demonstrated that KSA-101696 treatment can be tolerated very well by normal cells from different origin. Upon treatment of cells with 20 µM for 48 h, cells were stained with Annexin-V and PI and binding of Annexin-V and PI to the cells was determined by flow cytometry. The observed increase in apoptosis in cancer cells was significantly greater than that in normal cells (see FIGS. 2C-2D).

Thus, KSA-101696 is a selective and highly potent inhibitor of Notch that functions by activating the expression of the cell fate determinant Numb protein.

Example 3

Unless indicated otherwise, all methods mentioned in this example were carried out as described in Example 1.

Figure 3A:
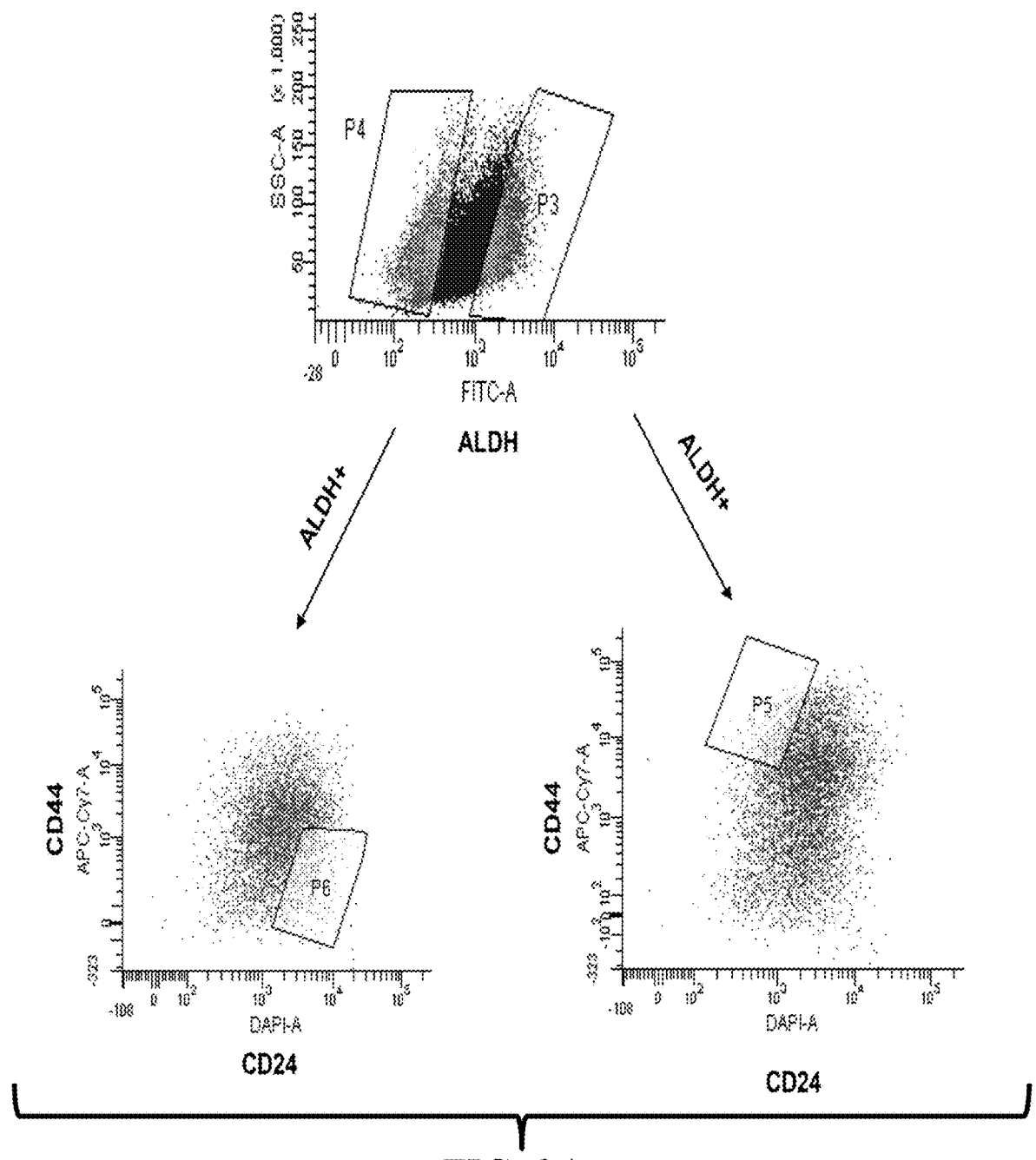
FIGS. 3A-3B show data from flow cytometry experiments to compare the efficiency of KSA-101696 to induce apoptosis in breast cancer stem cells and differentiated breast cancer cells.
Figure 3B:
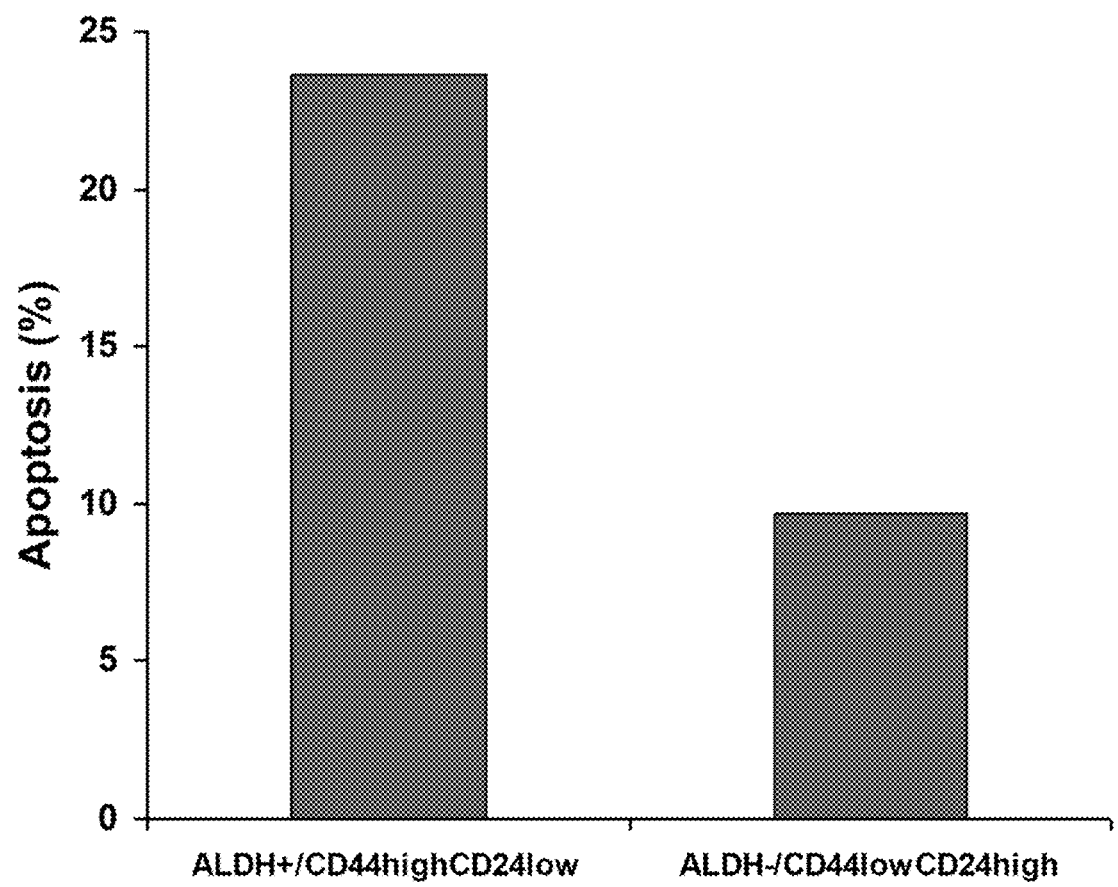

$ALDH^+$ $CD24^{low}/CD44^{High}$ breast cancer stem cells were sorted and cultured for 24 h. Cells were then treated with 10 µM of the compound KSA-101696 for two days. At the same time, $ALDH^-$ $CD24^{High}/CD44^{low}$ breast cancer differentiated cells were used as a negative control to evaluate the selective apoptotic activity of the compound against breast cancer stem cells compared with differentiated phenotype from the same bulk population of MDA-MB-468 cells. Treatment of cancer stem cells resulted in a two-fold increase of induced apoptosis compared to the differentiated breast cancer cells (see FIGS. 3 A and B).

Thus, KSA-101696 selectively induces apoptosis in cancer stem cells, but not in differentiated cells.

Example 4

Unless indicated otherwise, all methods mentioned in this example were carried out as described in Example 1.

It is known that one of the properties of stem/progenitor cells is their ability to survive under anchorage-independent conditions and generate mammospheres, which are composed of a small number of stem cells. Given that CSCs generally make up for a small minority of the cells within cancer cell populations, the dye DyeCycle Violet was used to isolate SP cells (side population cells; the side population is enriched for stem/progenitor cells), through a BD FACSAria™ cell sorter. Subsequently, the isolated SP cells were used in a Mammosphere Formation Assay. SP cells of MCF-7 and BT-474 formed more mammospheres than non-SP cells (see FIG. 4A).

Next, the effects of varying concentrations of the compound KSA-101696 on mammosphere formation was determined.

Figure 4A:
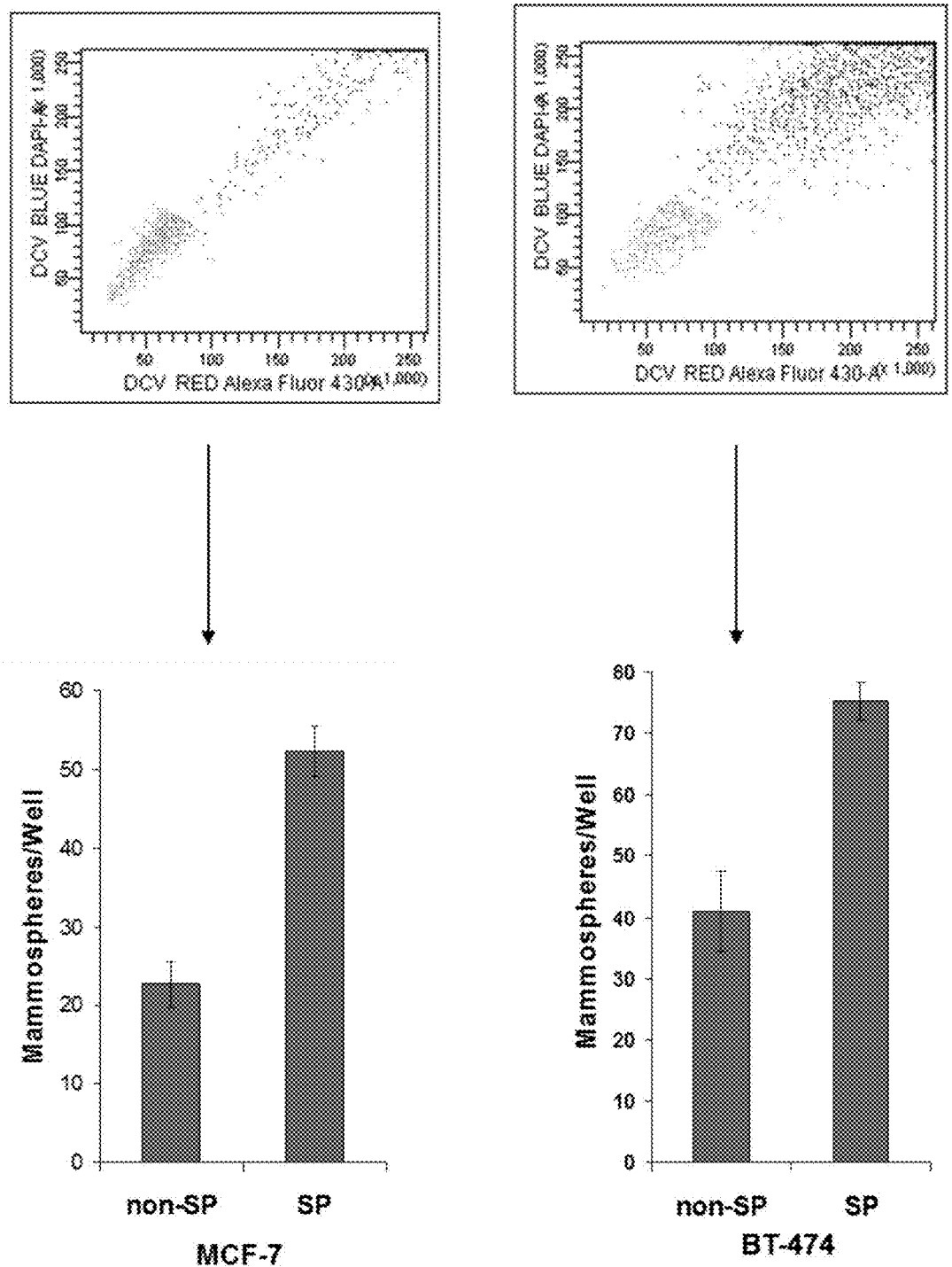
FIGS. 4A-4D show data obtained from tissue culture cells by flow cytometric analysis and microscopy in order to address the question if KSA-101696 affects the formation/survival of mammospheres and the fraction of side population cells.
Figure 4B:
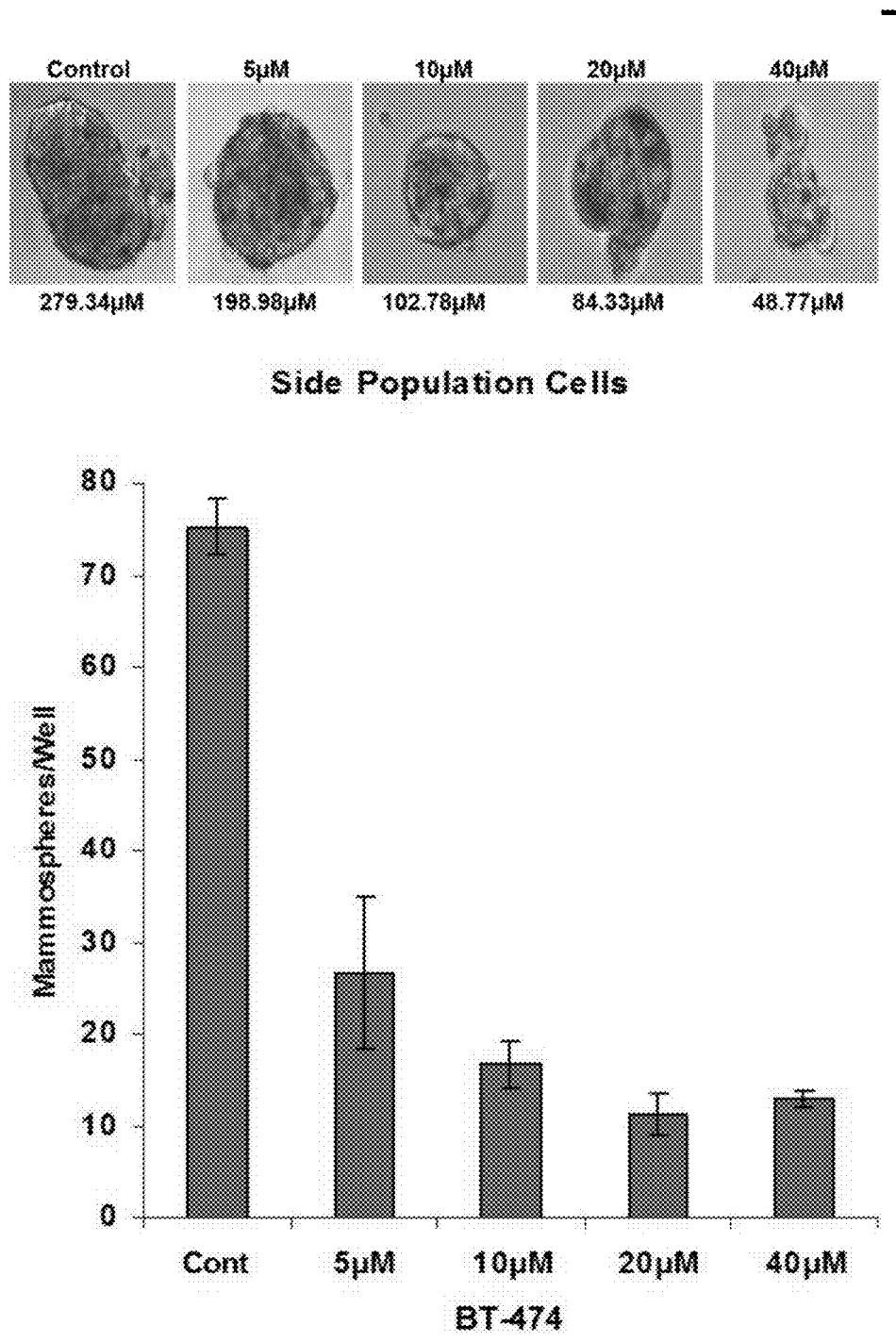
Figure 4C:
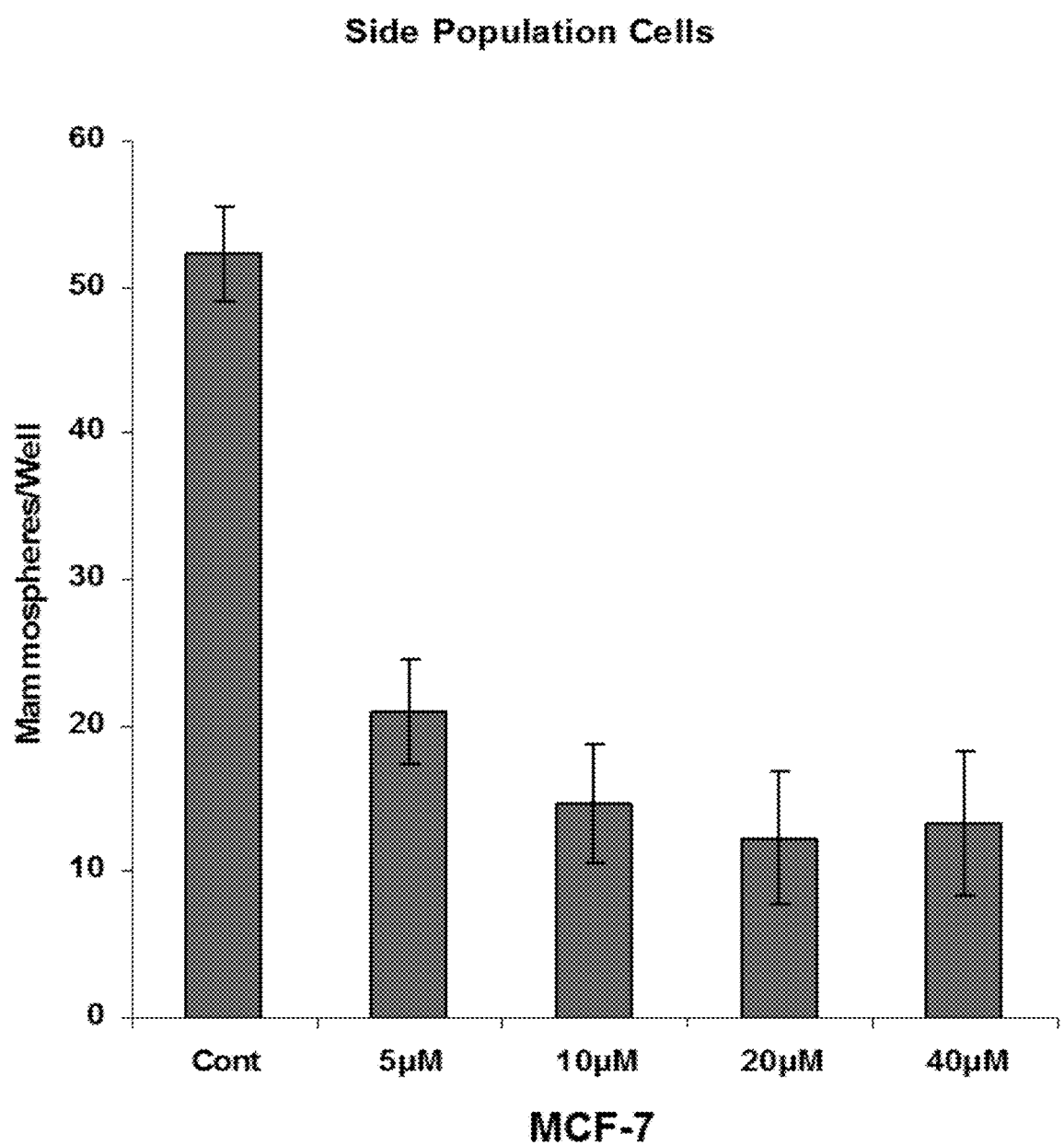

Treatment of 7 days old mammospheres of both cell lines with 5 µM of KSA-101696 decreased the number of mammospheres formed by 50% compared to DMSO treatment (FIG. 4A). Moreover, a reduction in the size of treated mammospheres was observed (FIG. 4B).

Figure 4D:
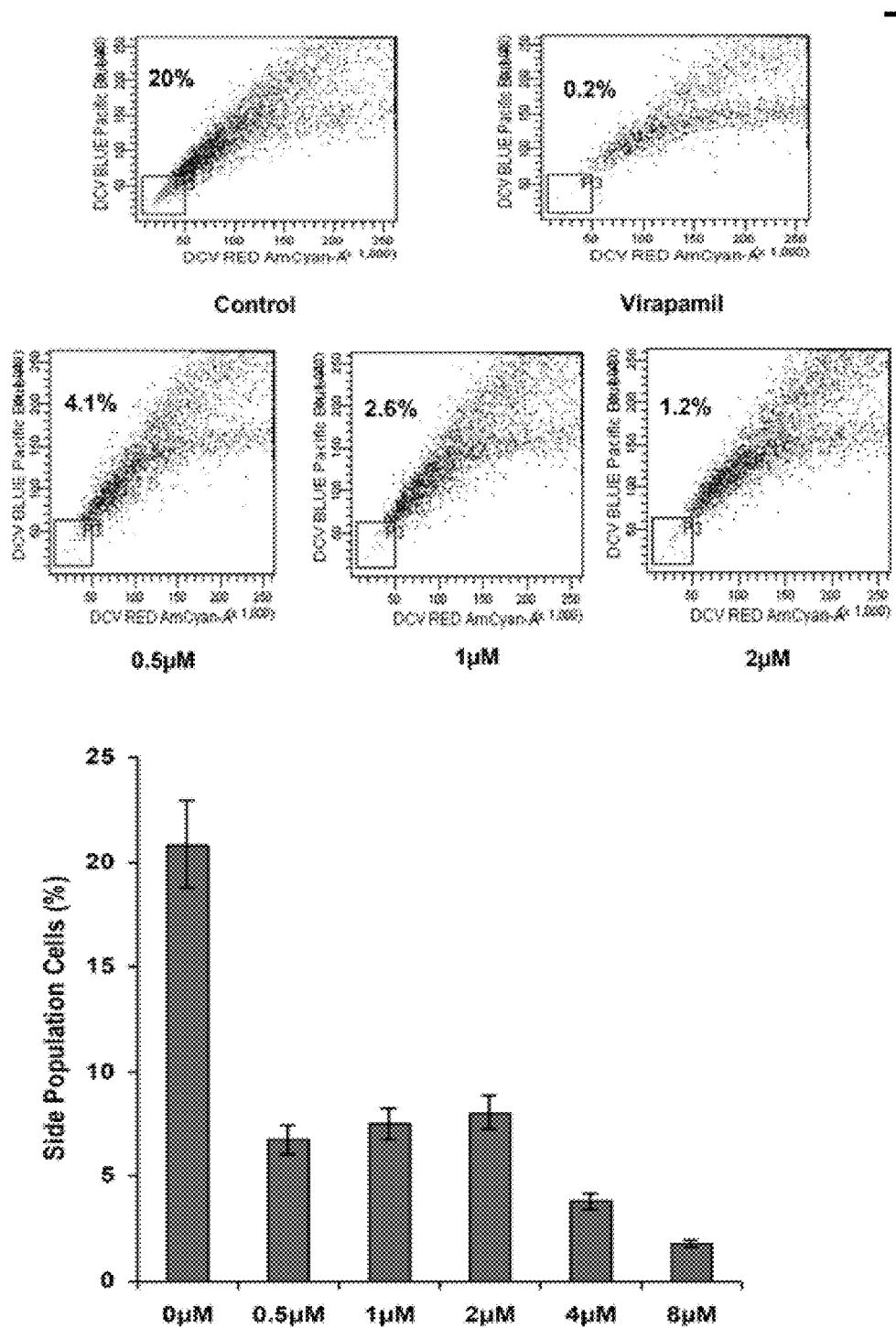

Next, the effects of the compound KSA-101696 in SP cells under normal culture conditions was evaluated. Upon treatment of MCF-7 cells with different concentrations of the compound KSA-101696 for 24 h, it was found that the compound is a potent SP cell inhibitor with $IC_{50} \approx 0.3$ µM (see FIG. 4D).

Thus, KSA-101696 reduces the size of the side population (i.e. the percentage of cells that belong to the side population), inhibits mammosphere formation of isolated SP Cells and reduces the sphere formation efficiency of these cells.

Example 5

Unless indicated otherwise, all methods mentioned in this example were carried out as described in Example 1.

The ALDEFLUOR assay has been suggested to fit the universality required for a stem cell marker that is reliable across species and tissues. Because SKBR3 cells include, among various cell lines tested, a particularly high percentage of ALDH-positive cells, SKBR3 cells were selected to evaluate whether KSA-101696 inhibits ALDH-positive cells in vitro.

Figure 5A:
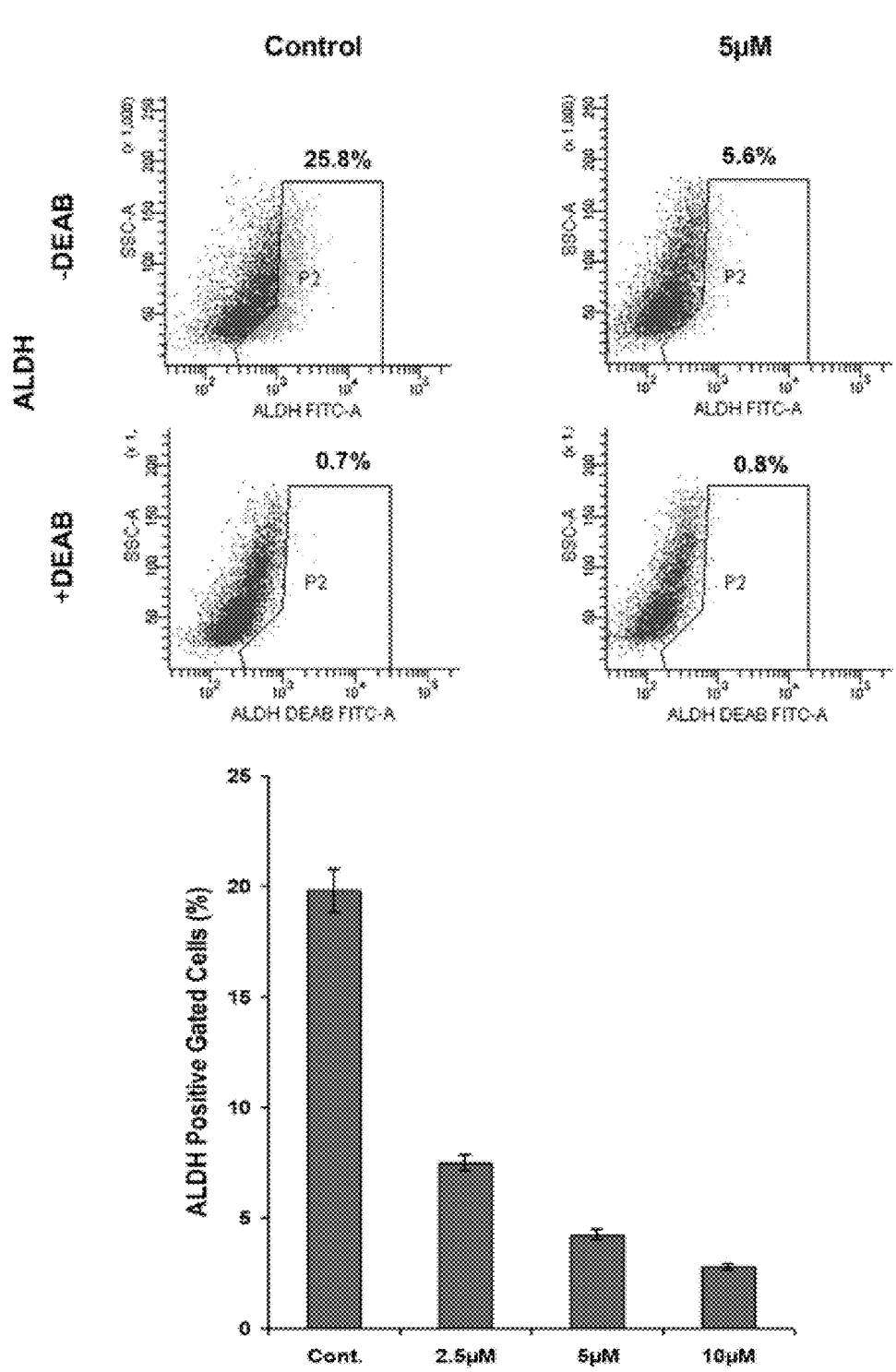
FIGS. 5A-5B show experimental data from flow cytometry experiments to examine if KSA-101696 has inhibitory effects on ALDH$^+$ cells in cultured cells (FIG. 5A) and affects colony formation by ALDH$^+$ cells (FIG. 5B).

After two days of treatment with 2.5 µM of KSA-101696, a more that 50% reduction in ALDH-positive cell percentage was observed (FIG. 5A). Consistently with the effect of the compound on mammosphere formation ability of breast cancer cells, the compound showed about the same effect on ALDH-positive cells with $IC_{50} \approx 2$ µM.

Figure 5B:
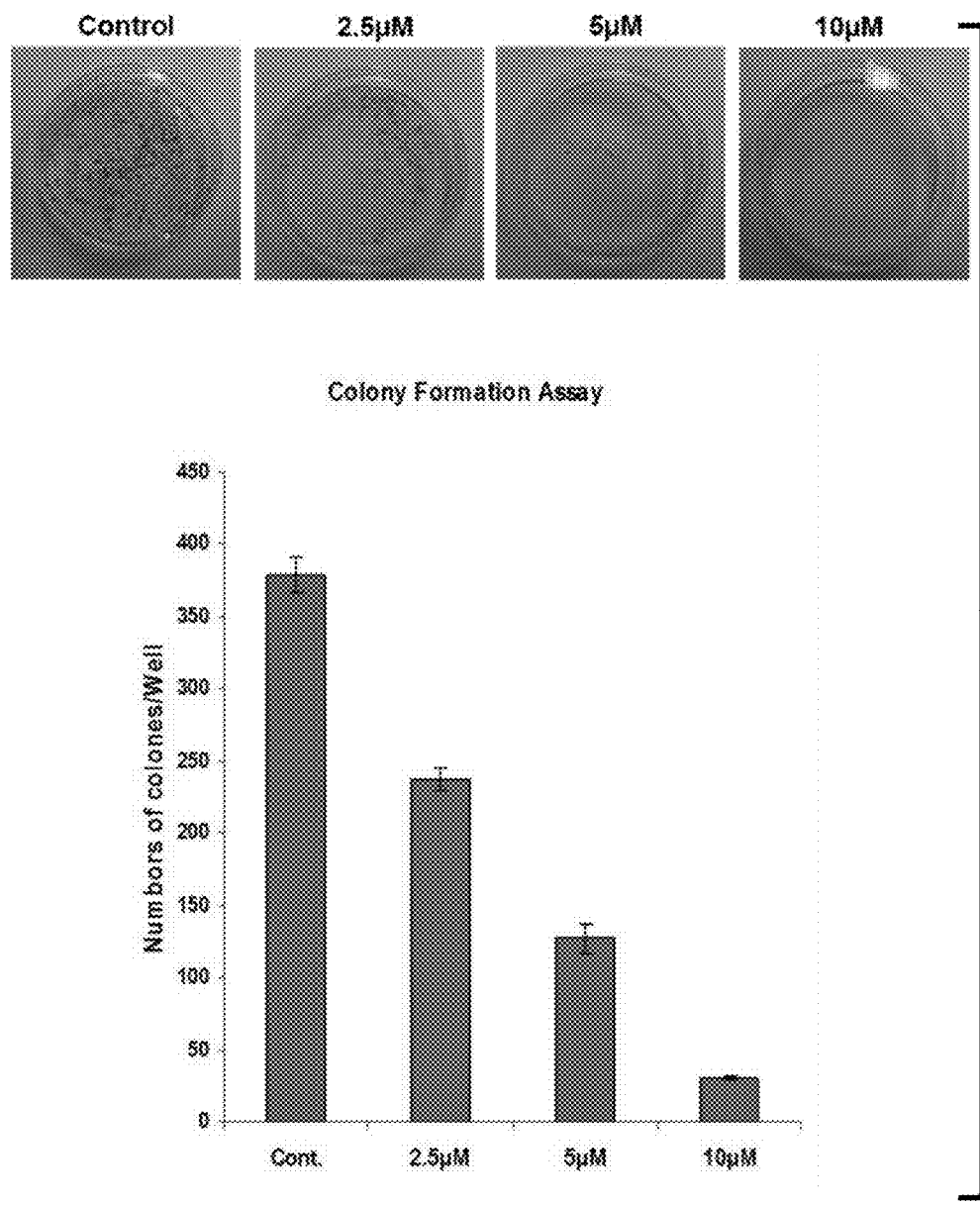

It has been shown that colony forming efficiency is significantly greater in ALDH-positive cells compared to ALDH-negative cells. Thus, from the same cells as used in the ALDEFLUOR assay, 5000 viable cells were seeded in a 60 mm tissue culture dish. In a direct relationship with the reduction in ALDH-positive cell population, the compound showed the same activity in inhibition of colony forming cells (see FIG. 5B).

Thus, KSA-101696 inhibits ALDH⁺ cells and colony forming efficiency in vitro.

Example 6

Unless indicated otherwise, all methods mentioned in this example were carried out as described in Example 1.

Breast cancer metastasis accounts for the majority of deaths from breast cancer. It has been proposed that CSCs play a crucial role in cancer metastasis. Therefore targeting cancer stem cells may allow to block the roots of the metastatic process and may thus be an attractive strategy to treat and control metastatic tumors.

Treatment of highly metastasized MDA-MB-231 cells with different concentrations of KSA-101696 ranging from 2.5 µM to 20 µM blocked the migration capacity of the cancer cells with $IC_{50} \approx 7.5$ µM (FIG. 6A).

To get successful metastasis cancer cells must have the ability to invade the surrounding cells, thus inhibition of cell invasion is a choice to block one of the important steps in metastasis. KSA-101696 showed potency to inhibit cancer cell invasion with an $IC_{50}$ similar to the dose that inhibited migration by 50% (see FIG. 6B).

From these experiments, it can be seen that KSA-101696 blocks the metastasis process at multiple steps, which makes the compounds a potent inhibitor of cancer cell and cancer stem cell-driven metastasis.

Example 7

Unless indicated otherwise, all methods mentioned in this example were carried out as described in Example 1.

Figure 7A:
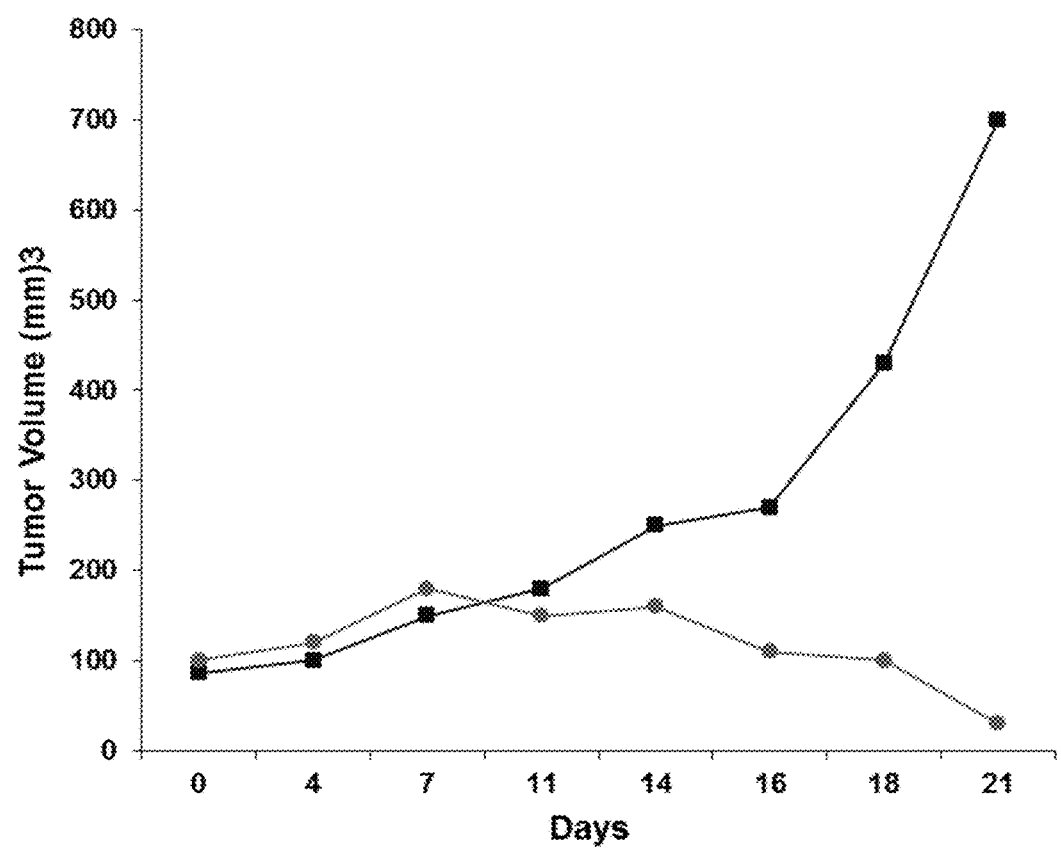
FIGS. 7A-7B show in vivo data obtained from mice to study the effects of KSA-101696 on tumor volume (FIG. 7A) and examine potential side effects associated with KSA-101696 (FIG. 7B).
Figure 7B:
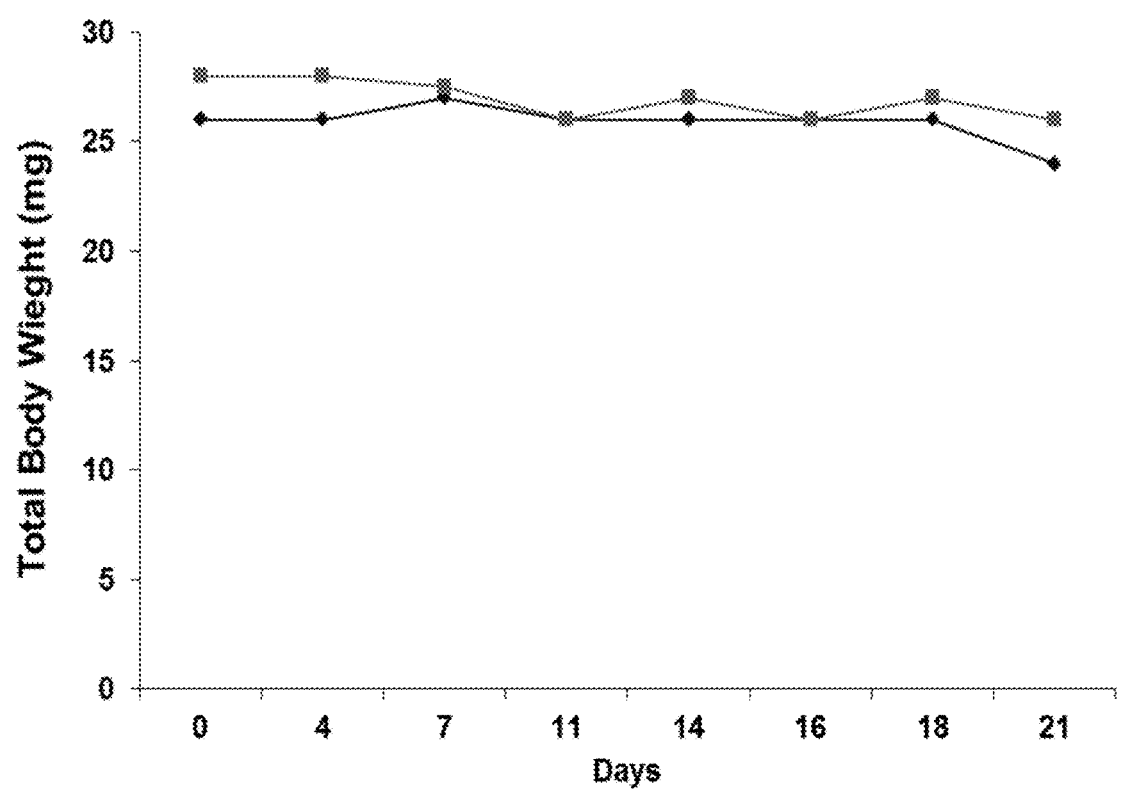

Because of the observed selective cytotoxic effect of compound KSA-101696 against cancer cells and the tolerance of normal cells and normal stem cells in vitro, a high dose of compound KSA-101696 (200 mg/kg) was used on mice. The treatment of mice bearing MDA-MB-468 tumors resulted in a reduction (shrinking) of tumor volume by 70% after three doses of the compound via intraperitoneal administration (see FIG. 7A; circles: KSA-101696 treatment; squares: vehicle control. The treatment resulted in no measurable weight loss (FIG. 7B; circles: KSA-101696 treatment; squares: vehicle control) or any other sign of general toxicity (in particular no convulsions, CNS stimulation, diarrhea, increased urination, miosis or mydriasis).

Example 8

Unless indicated otherwise, all methods mentioned in this example were carried out as described in Example 1.

This experiment was carried out with three breast cancer cell lines: MDA-MB-468, SKBR-3 and T47D. The MDA-MB-468 cell line represents the basal like breast cancer (which is a breast cancer subtype with a more aggressive clinical behavior). The SKBR-3 cell line represents Her-2 overexpressing breast cancer. Both cell lines exhibit stem cell character and resistance to chemotherapy. The T47D cell line represents ER/PR positive breast cancer. Unlike MDA-MB-468 cells or SKBR-3 cells, T47D cells are highly differentiated cells and respond very well to hormonal therapy and chemotherapy.

Figure 9A:
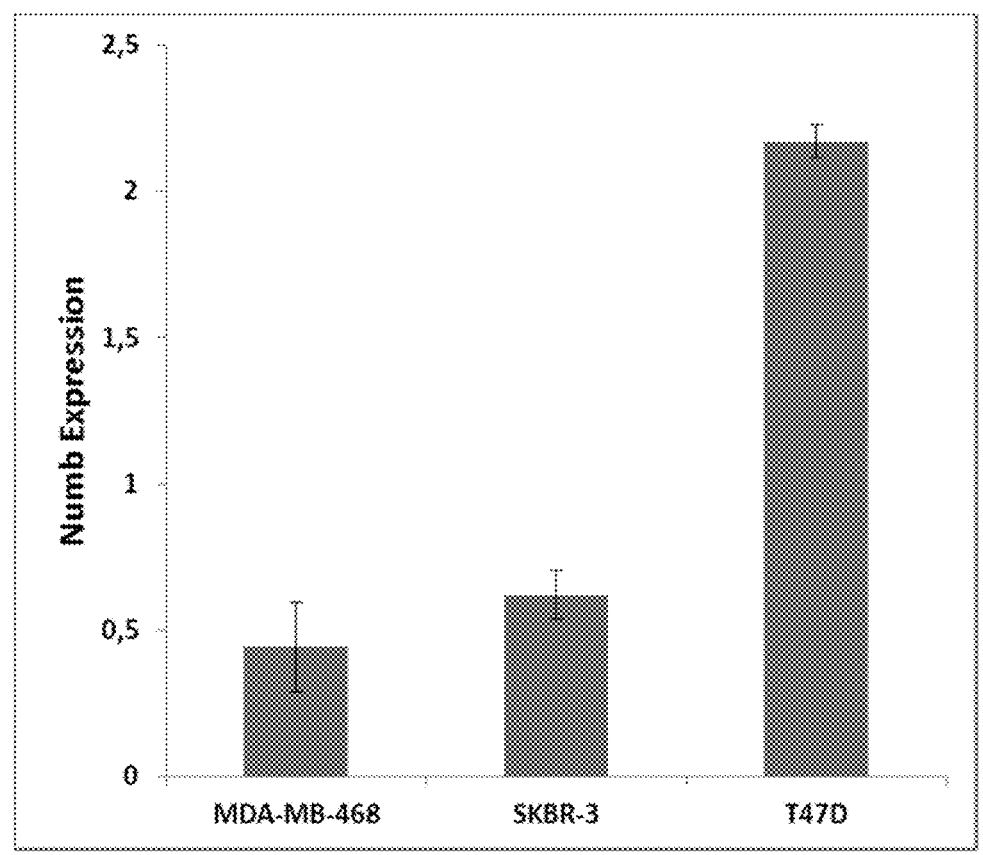

As seen from FIG. 9A, quantification of chemoluminescence in western blotting showed reduced levels of p-Numb, the active form of Numb protein, in MDA-MB-468 cells (GADPH protein was used as control for normalization within each cell line). Similarly, SKBR-3 cells showed reduced levels of p-Numb. In contrast, T47D cells showed increased levels of p-Numb.

In a next step, it was investigated whether there was a correlation between Numb protein expression and sensitivity of a cell line to the apoptotic effects of KSA-101696. Apoptotic cells were determined by Annexin-V staining as described in Example 1.

As can be seen from FIG. 9B, KSA-101696 increased apoptosis in breast cancer cell lines showing low levels of Numb expression (MDA-MB-468 and SKBR-3), while it did not have such effects in the cell line showing high Numb expression (T47D).

Example 9

Unless indicated otherwise, all methods mentioned in this example were carried out as described in Example 1.

In this experiment, the $LD_{50}$ values for KSA-101696 and doxorubicin were measured with mice as described in Example 1, section "Determination of $LD_{50}$ Value".

Results are shown in Table 1 below.

TABLE 1

|  | $ED_{50}$ | $LD_{50}$ | Therapeutic ratio |
| --- | --- | --- | --- |
| KSA-101696 | 50 mg/kg | 2000 mg/kg | 40 |
| Doxorubicin | nd | 60 mg/kg |  |

The route of administration is intraperitoneal.
$LD_{50}$ is the dose that killed 50% of the animal within 72 h.
$ED_{50}$ is the dose that shrinks the tumor volume by 50% at the end of treatment.
Therapeutic ratio = $LD_{50}/ED_{50}$
nd: Not determined Example 10

All methods mentioned in this example were carried out as described in Example 1. The Effect of KSA-101696 on hematopoietic progenitor leukemic cells Injection of CD34⁺ hematopoietic stem cells has been clinically applied to treat various diseases including spinal cord injury, liver cirrhosis and peripheral vascular disease. Acute myeloid leukemia (AML) arises from a rare subpopulation of leukemia stem cells (LSCs), originating from malignant transformation of hematopoietic stem cells (HSCs) or progenitors. AML represents a heterogeneous group of malignant stem cell diseases in which CD34⁺ blast cells are frequently identified. Enhanced expression of anti-apoptotic markers and MDR1 has been associated with CD34 expression, immature French-American-British (FAB) subtypes, and unfavorable karyotypes, as well as with low complete remission and/or survival rates. Interestingly, in AML and myelodysplastic syndromes, the number of CD34⁺ blast cells is higher in the advanced stages of the disease and at relapse. This suggests that CD34⁺ blast cells are particularly resistant to chemotherapy and less susceptible to apoptosis.

THP-1 leukemic cells were cultured in RPMI medium in 25 mm flask and treated with KSA-101696 for 48 h. Cells were then washed and stained with anti-CD34-FITC (BD biosciences) for 30 min at room temperature. The hematopoietic stem cell population (CD34 positive cells) was analyzed by flow cytometry to evaluate the effect of KAS-101696 on hematopoietic stem cells of leukemic origin. Upon treatment with KSA-101696 the CD34 positive cell population was decreased, thus demonstrating an inhibitory effect of KSA-101696 in cancer stem cells of hematological origin.

Figure 10A:
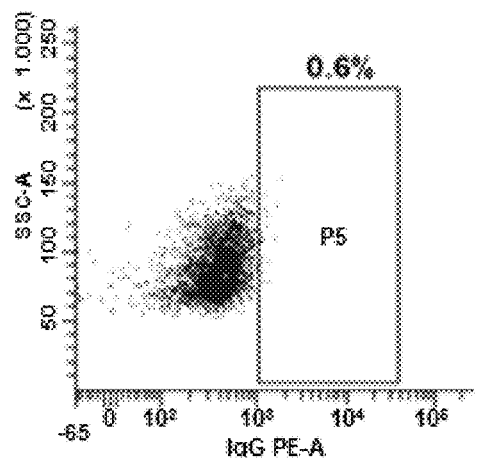
FIGS. 10A-10B show data obtained by flow cytometry to study the effects of KSA-101696 on hematopoietic progenitor leukemic cells.
Figure 10A:
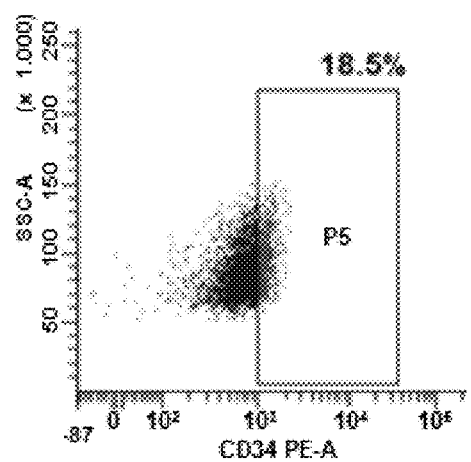
Figure 10A:
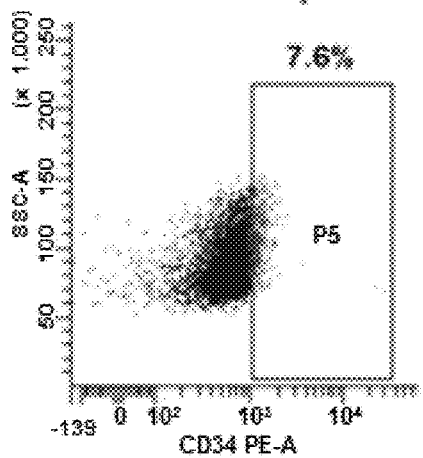
Figure 10A:
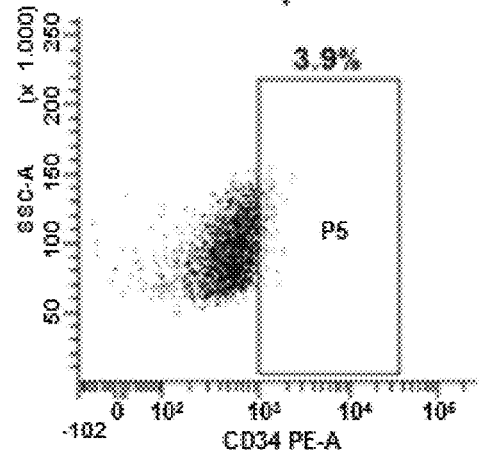
Figure 10B:
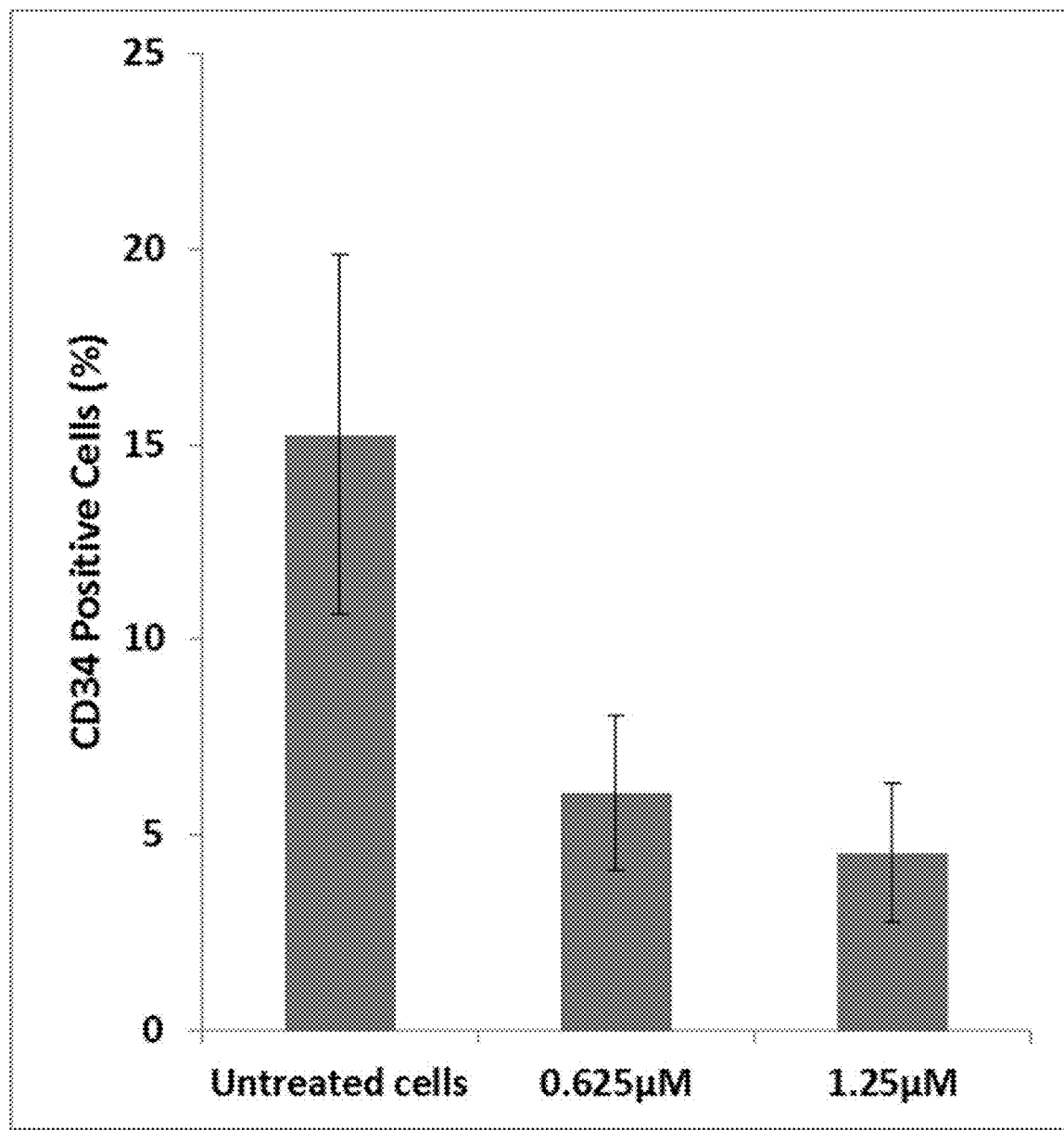

KSA-101696 treatment on THP-1 acute monocytic leukemia cells resulted in reduction of CD34+ cells percentage (see FIGS. 10A and B).

Example 11

Unless indicated otherwise, all methods mentioned in this example were carried out as described in Example 1.

Figure 11:
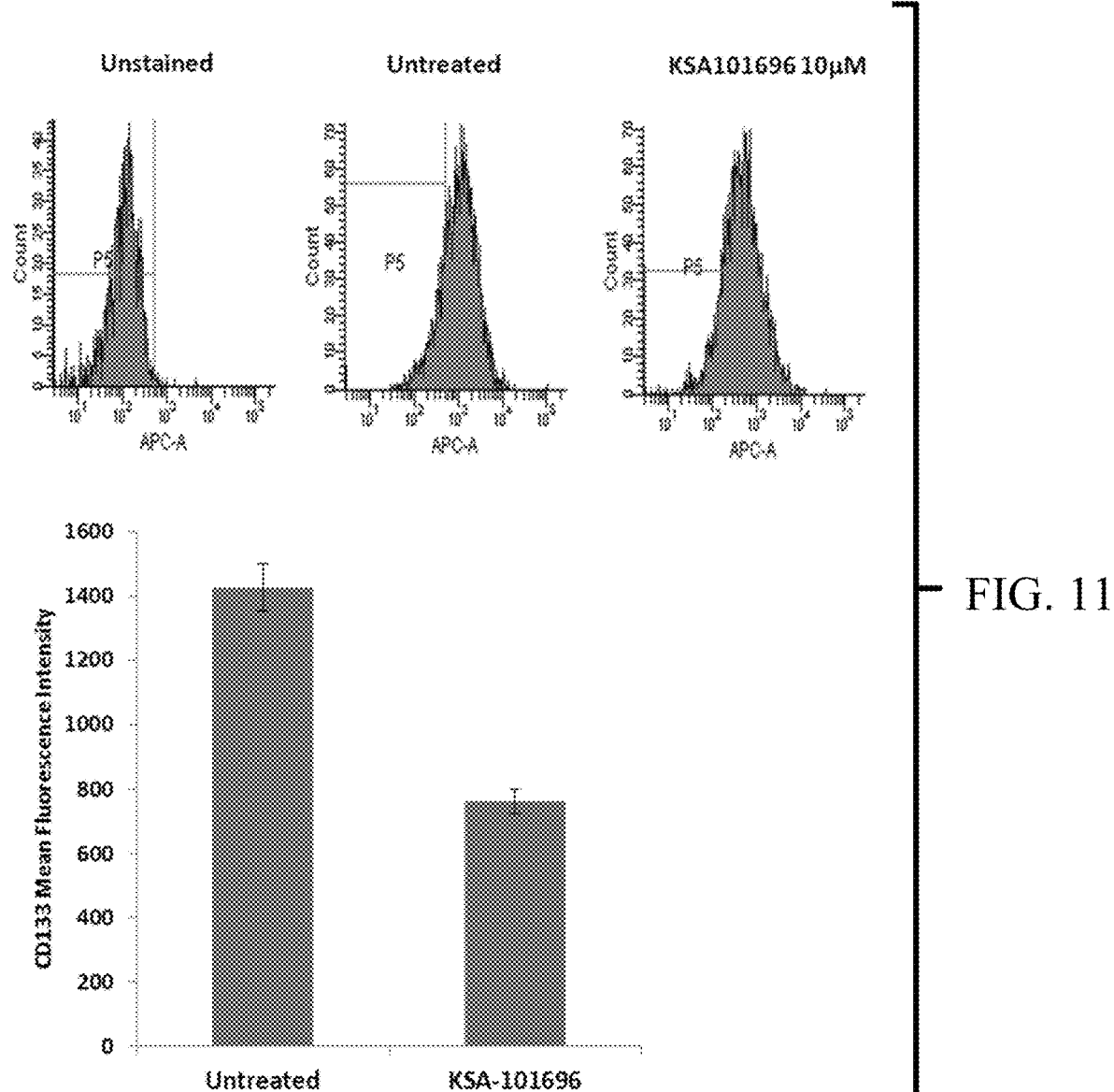
FIG. 11 shows data obtained by flow cytometry (anti-CD133 antibody) to study the effects of KSA-101696 on colon cancer cells (HT-29).

In a further experiment, HT-29 colon cancer cells were cultured in 6 well plates and treated by KSA-101696 (10 μM) or vehicle for 48 h. Then, cells were collected and stained with a CD133 antibody and analyzed by flow cytometry. The analysis showed inhibition in the expression of the colon cancer stem cell marker CD133 in the treated cells (see FIG. 11).

Example 12

Unless indicated otherwise, all methods mentioned in this example were carried out as described in Example 1.

Figure 12:
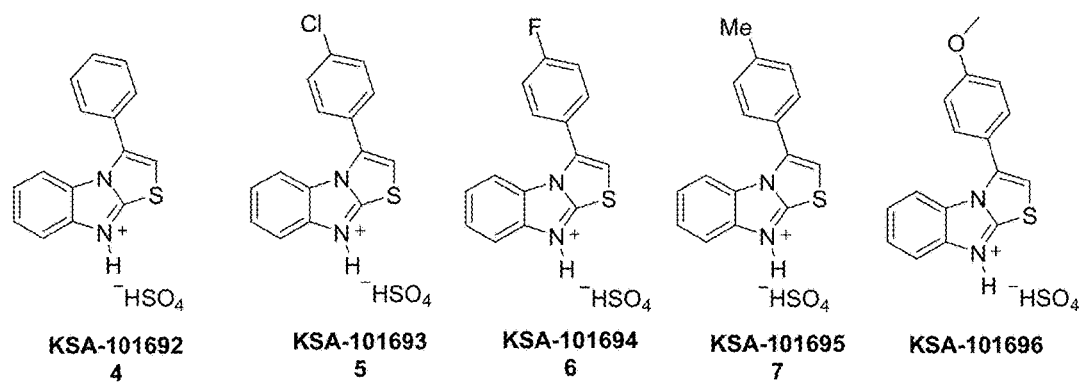
FIG. 12 shows the structures of several compounds related to KSA-101696.
Figure 13:
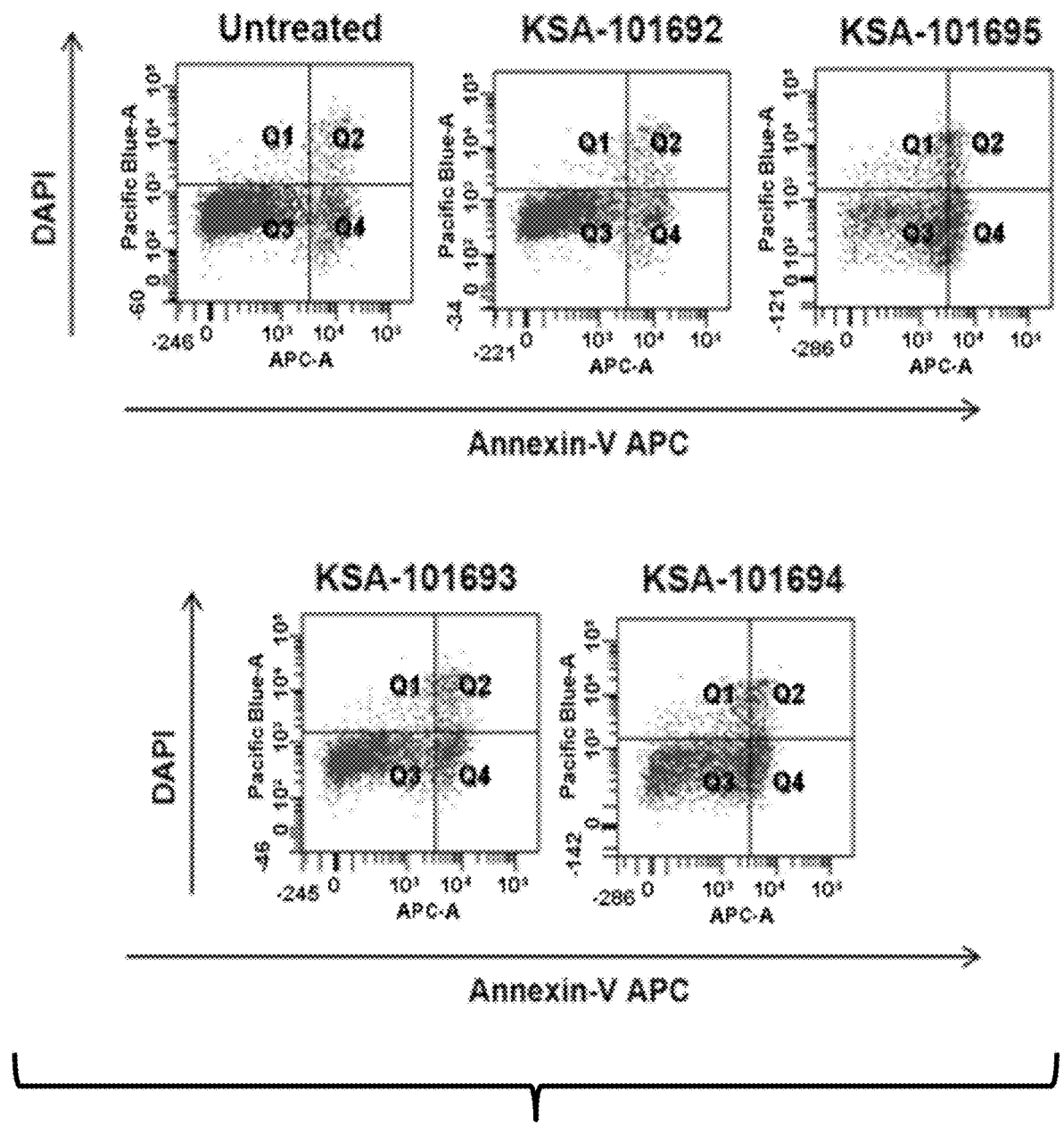
FIG. 13 SKBr-3 cells were harvested after treatment by the indicated compounds for 48 h and incubated with annexin V-APC and DAPI. Ten thousand cells were analyzed per determination. Dot plots show Annexin V-APC binding on the X axis and DAPI staining on the Y axis. Dots represent cells as follows: lower left quadrant, normal cells (APC$^-$/DAPI$^-$); lower right quadrant, apoptotic cells (APC$^+$/DAPI$^-$); upper left quadrant, necrotic cells (APC$^-$/PI$^+$).

In a further experiments, the compounds KSA-101692 (4), KSA-101693 (5), KSA-101694 (6) and KSA-101695 (7) (for chemical structure see FIG. 12) were tested for their anticancer activity by induced cell programmed death apoptosis on breast cancer cell line SKBr-3.

It was found that KSA-101693 (5), KSA-101694 (6) and KSA-101695 (7) showed induced cell programmed death apoptosis on breast cancer cells. However, low activity was measured on breast cancer cells treated by KSA-101692 (4).

The features of the present invention disclosed in the specification, the claims, and/or in the accompanying drawings may, both separately and in any combination thereof, be material for realizing the invention in various forms thereof.

REFERENCES

Al-Hajj, M., Wicha, M. S., Benito-Hernandez, A., Morrison, S. J. & Clarke, M. F. Prospective identification of tumorigenic breast cancer cells. *Proc Natl Acad Sci USA* 100, 3983-3988, doi:10.1073/pnas.0530291100 0530291100 [pii] (2003).
Charafe-Jauffret, E. et al. Aldehyde dehydrogenase 1-positive cancer stem cells mediate metastasis and poor clinical outcome in inflammatory breast cancer. *Clin Cancer Res* 16, 45-55, doi:1078-0432.CCR-09-1630 [pii] 10.1158/1078-0432.CCR-09-1630 (2010).
Dontu, G. et al. In vitro propagation and transcriptional profiling of human mammary stem/progenitor cells. *Genes Dev* 17, 1253-1270, doi:10.1101/gad.1061803 17/10/1253 [pii] (2003).
Frank, N. Y. et al. The therapeutic promise of the cancer stem cell concept. *J Clin Invest.* 120(1), 41-50. doi: 10.1172/JCI41004 (2010).
Ginestier, C. et al. ALDH1 is a marker of normal and malignant human mammary stem cells and a predictor of poor clinical outcome. *Cell Stem Cell* 1, 555-567, doi: S1934-5909(07)00133-6 [pii] 10.1016/j.stem.2007.08.014 (2007).
Kondo, T., Setoguchi, T. & Taga, T. Persistence of a small subpopulation of cancer stem-like cells in the C6 glioma cell line. *Proc Natl Acad Sci USA* 101, 781-786, doi:10.1073/pnas.0307618100 0307618100 [pii] (2004).
Li, X. et al. Intrinsic resistance of tumorigenic breast cancer cells to chemotherapy. *J Natl Cancer Inst* 100, 672-679, doi:djn123 [pii] 10.1093/jnci/djn123 (2008).
McDermott, S. P. & Wicha, M. S. Targeting breast cancer stem cells. *Mol Oncol* 4, 404-419, doi:10.1016/j.molonc.2010.06.005 S1574-7891(10)00051-7 [pii] (2010).
Morimoto, K. et al. Stem cell marker aldehyde dehydrogenase 1-positive breast cancers are characterized by negative estrogen receptor, positive human epidermal growth factor receptor type 2, and high Ki67 expression. *Cancer Sci* 100, 1062-1068, doi:CAS1151 [pii] 10.1111/j.1349-7006.2009.01151.x (2009).
Patrawala, L. et al. Side population is enriched in tumorigenic, stem-like cancer cells, whereas ABCG2+ and ABCG2− cancer cells are similarly tumorigenic. *Cancer Res* 65, 6207-6219, doi:65/14/6207 [pii] 10.1158/0008-5472.CAN-05-0592 (2005).
Tanei, T. et al. Association of breast cancer stem cells identified by aldehyde dehydrogenase 1 expression with resistance to sequential Paclitaxel and epirubicin-based chemotherapy for breast cancers. *Clin Cancer Res* 15, 4234-4241, doi:1078-0432.CCR-08-1479 [pii] 10.1158/1078-0432.CCR-08-1479 (2009).
Yu, F. et al. let-7 regulates self renewal and tumorigenicity of breast cancer cells. *Cell* 131, 1109-1123, doi:S0092-8674(07)01417-1 [pii] 10.1016/j.cell.2007.10.054 (2007).

We claim:
1. A method of treatment of cancer selected from breast cancer and leukemia comprising the administration of a benzo-thiazolo-imidazole compound to a human patient in need thereof, said compound having the structure represented by Formula I:

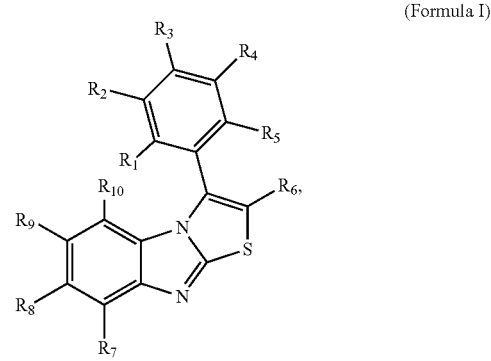

(Formula I)

wherein
R$_1$, R$_2$, R$_4$ and R$_5$ are independently selected from the group consisting of
hydrogen,
halogen,
hydroxyl,
amino, which is unsubstituted or substituted,
nitro,
cyano,
thiol,
sulfonyl,
rbonyl,
carboxyl,
straight or branched alkyl, which is unsubstituted or substituted,
straight or branched alkoxy, which is unsubstituted or substituted, straight or branched alkenyl, which is unsubstituted or substituted,
substituted or unsubstituted cycloalkyl, and
substituted or unsubstituted aryl or heteroaryl,
wherein, each of $R_1$, $R_2$, $R_4$ and $R_5$ comprises up to 18 carbon atoms,
$R_3$ is selected from the group consisting of
hydrogen,
halogen,
hydroxyl,
amino, which is unsubstituted or substituted,
nitro,
cyano,
thiol,
sulfonyl,
carbonyl,
carboxyl,
straight or branched alkyl, which is unsubstituted or substituted,
straight or branched alkoxy, which is unsubstituted or substituted,
straight or branched alkenyl, which is unsubstituted or substituted,
substituted or unsubstituted cycloalkyl, and
substituted or unsubstituted aryl or heteroaryl,
wherein, $R_3$ comprises up to 18 carbon atoms,
$R_6$ is selected from the group consisting of
hydrogen,
halogen,
hydroxyl,
amino, which is unsubstituted or substituted,
nitro,
cyano,
thiol,
sulfonyl,
straight or branched alkyl, which is unsubstituted or substituted, wherein any substituents are selected from the group consisting of halogen, hydroxyl, amino, nitro, cyano, thiol, sulfonyl, alkyl, alkoxy, alkenyl, cycloalkyl, aryl and heteroaryl,
straight or branched alkoxy, which is unsubstituted or substituted,
straight or branched alkenyl, which is unsubstituted or substituted,
substituted or unsubstituted cycloalkyl, and
substituted or unsubstituted aryl or heteroaryl,
wherein, $R_6$ comprises up to 18 carbon atoms;
$R_7$, $R_8$, $R_9$ and $R_{10}$ are independently selected from the group consisting of
hydrogen,
halogen,
hydroxyl,
amino, which is unsubstituted or substituted,
nitro,
cyano,
thiol,
sulfonyl,
carbonyl,
carboxyl,
straight or branched alkyl, which is unsubstituted or substituted,
straight or branched alkoxy, which is unsubstituted or substituted,
straight or branched alkenyl, which is unsubstituted or substituted,
substituted or unsubstituted cycloalkyl, and
substituted or unsubstituted aryl or heteroaryl, wherein, each of $R_7$, $R_8$, $R_9$ and $R_{10}$ comprises up to 18 carbon atoms or a pharmaceutically acceptable salt thereof.

2. The method according to claim 1, wherein said benzothiazolo-imidazole compound has the structure represented by Formula I:

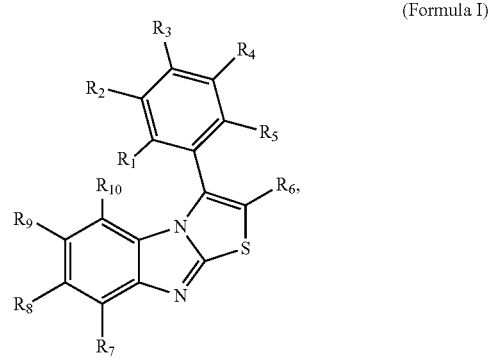

(Formula I)

wherein $R_1$, $R_2$, $R_4$ and $R_5$ are independently selected from the group consisting of hydrogen, halogen, straight or branched alkyl, which is unsubstituted, wherein, each of $R_1$, $R_2$, $R_4$ and $R_5$ comprises up to 4 carbon atoms, and wherein at least two of the four groups $R_1$, $R_2$, $R_4$ and $R_5$ are hydrogen, $R_3$ is selected from the group consisting of hydrogen, halogen, hydroxyl, straight or branched alkoxy, which is unsubstituted, wherein $R_3$ comprises up to 4 carbon atoms $R_6$ is selected from the group consisting of hydrogen, halogen, straight or branched alkyl, which is unsubstituted, wherein $R_6$ comprises up to 4 carbon atoms;

$R_7$, $R_8$, $R_9$ and $R_{10}$ are independently selected from the group consisting of hydrogen, halogen, straight or branched alkyl, which is unsubstituted, wherein each of $R_7$, $R_8$, $R_9$ and $R_{10}$ comprises up to 4 carbon atoms, and wherein at least two of the four groups $R_7$, $R_8$, $R_9$ and $R_{10}$ are hydrogen; or a pharmaceutically acceptable salt thereof.

3. The method according to claim 1, wherein said benzothiazolo-imidazole compound has the structure represented by Formula II:

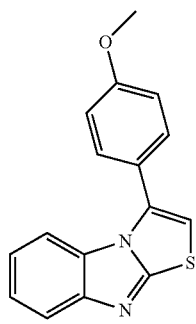
(Formula II)

or a pharmaceutically acceptable salt thereof.

4. The method according to claim 1, wherein said benzo-thiazolo-imidazole compound or pharmaceutically acceptable salt thereof is administered in a pharmaceutical composition comprising at least one pharmaceutically acceptable carrier, diluent, and/or excipient.

5. The method according to claim 1, wherein the breast or leukemia cancer cells are characterized by a decreased expression level of the protein Numb, compared to non-cancerous cells.

6. The method, according to claim 5, wherein the cells of said cancer are characterized by a decreased expression level of the protein Numb, compared to non-cancerous cells of the same cell type from the same subject, wherein said decrease in the expression level of the protein Numb is a decrease by at least 20%.

7. The method according to claim 1, wherein said benzo-thiazolo-imidazole compound or pharmaceutically acceptable salt thereof is administered by intravenous injection or by ingestion.

8. The method according to claim 1, wherein said benzo-thiazolo-imidazole compound or pharmaceutically acceptable salt thereof is administered to said patient at a dosage resulting in a dosage of said benzo-thiazolo-imidazole compound or pharmaceutically acceptable salt thereof in the range of from 1 to 200 mg/(kg*day).

9. The method according to claim 1, wherein simultaneously to said administration of said benzo-thiazolo-imidazole compound or pharmaceutically acceptable salt thereof, an effective amount of a chemotherapeutic agent selected from the group consisting of paclitaxel, doxyrubicin, vinblastine, vincristine, vinorelbine, topotecan, carboplatin, cisplatin, pemetrexed, irinotecan, gemcitabine, gefitinib, erlotinib, etoposide, fluorouracil, cyclophosphamide, mercaptopurine, fludarabine, ifosfamide, procarbazine and mitoxantrone is administered to said patient.

10. The method, according to claim 1, wherein each of $R_1$, $R_2$, $R_4$ and $R_5$ is hydrogen and $R_3$ is methoxy or halogen.

11. The method, according to claim 10, wherein R3 is methoxy.

12. The method, according to claim 1, wherein each of $R_6$, $R_7$, $R_8$, $R_9$ and $R_{10}$ is hydrogen.

13. A method of using a benzo-thiazolo-imidazole compound or pharmaceutically acceptable salt thereof, said compound or pharmaceutically acceptable salt thereof as defined in claim 1, for the manipulation of cultured cells, wherein said method comprises administration of said compound or pharmaceutically acceptable salt thereof to said cultured cells by including it in, or adding it to, a culture medium used for cultivation of said cultured cells, wherein the cultured cells are human breast cancer cells or leukemic cells.

14. The method, according to claim 13, wherein said manipulation is the induction of apoptosis and/or the induction of cell cycle arrest.

* * * * *

UNITED STATES PATENT AND TRADEMARK OFFICE
CERTIFICATE OF CORRECTION

| | | |
|---|---|---|
| PATENT NO. | : 10,550,130 B2 | Page 1 of 1 |
| APPLICATION NO. | : 15/071945 | |
| DATED | : February 4, 2020 | |
| INVENTOR(S) | : Abdullah Omar Al-Dhfyan et al. | |

It is certified that error appears in the above-identified patent and that said Letters Patent is hereby corrected as shown below:

In the Specification

Column 24,

Lines 27-30, "

TABLE 1

| | $ED_{50}$ | $LD_{50}$ | Therapeutic ratio |
|---|---|---|---|
| KSA-101696 | 50 mg/kg | 2000 mg/kg | 40 |
| Doxorubicin | nd | 60 mg/kg | |

" should read

Table 1:

| | $ED_{50}$ | $LD_{50}$ | Therapeutic ratio |
|---|---|---|---|
| KSA-101696 | 50 mg/kg | 2000 mg/kg | 40 |
| Doxorubicin | nd | 60 mg/kg | 20 |

--.

Signed and Sealed this
Nineteenth Day of May, 2020

Andrei Iancu
*Director of the United States Patent and Trademark Office*